United States Patent [19]

Franchini et al.

[11] Patent Number: 5,223,423
[45] Date of Patent: Jun. 29, 1993

[54] CHARACTERIZATION OF REPLICATION COMPETENT HUMAN IMMUNODEFICIENCY TYPE 2 PROVIRAL CLONE HIV-2$_{SBL/ISY}$

[75] Inventors: Genoveffa Franchini, Washington, D.C.; Flossie Wong-Staal, San Diego, Calif.; Robert Gallo, Bethesda, Md.

[73] Assignee: United States of America, Washington, D.C.

[21] Appl. No.: 331,212

[22] Filed: Mar. 31, 1989

[51] Int. Cl.$^5$ .................. C12N 15/49; C12N 7/02; C12N 7/04; C07H 21/04
[52] U.S. Cl. .................. 435/236; 435/235.1; 536/23.5; 930/221; 935/1; 935/6; 935/9; 935/11; 935/19
[58] Field of Search ........... 435/235.1, 172.1, 236; 536/27; 935/1; 530/350, 300, 324

[56] References Cited
PUBLICATIONS

Guyader, M. et al (1987) Nature 326, 662–669.
Albert, J. et al (1987) AIDS Res. and Human Retroviruses 3, 3–10.
Franchini, G. et al (1987) AIDS Res. and Human Retroviruses 3, 11–17.
Nicol, I. et al (1989) Intervirology 30, 258–267.

*Primary Examiner*—Richard A. Schwartz
*Assistant Examiner*—Johnny F. Railey, II
*Attorney, Agent, or Firm*—Cushman, Darby & Cushman

[57] ABSTRACT

A complete genomic clone of HIV-2 designated HIV-2$_{SBL/ISY}$ was cloned from DNA of the neoplastic human cell line HUT78 infected with the HIV-2$_{SBL6669}$ viral isolate. The clone was sequenced and the sequence compared with those of known HIV-2 isolates. The invention is advantageous for it provides an animal model for the study of HIV infection in man.

3 Claims, 31 Drawing Sheets

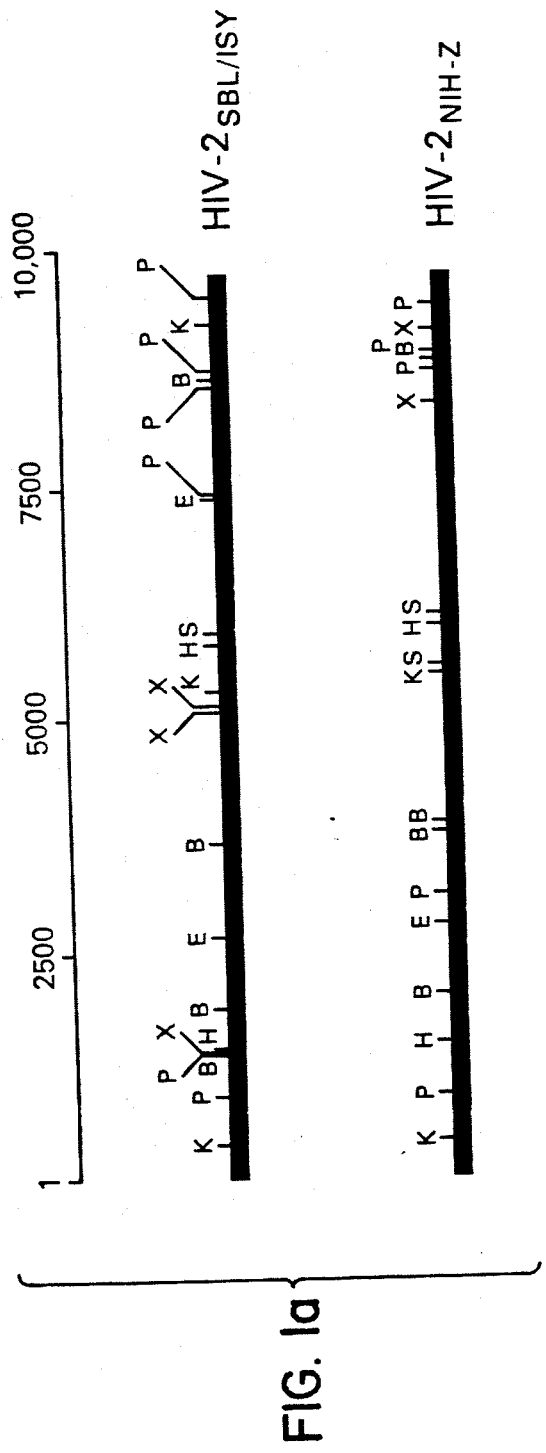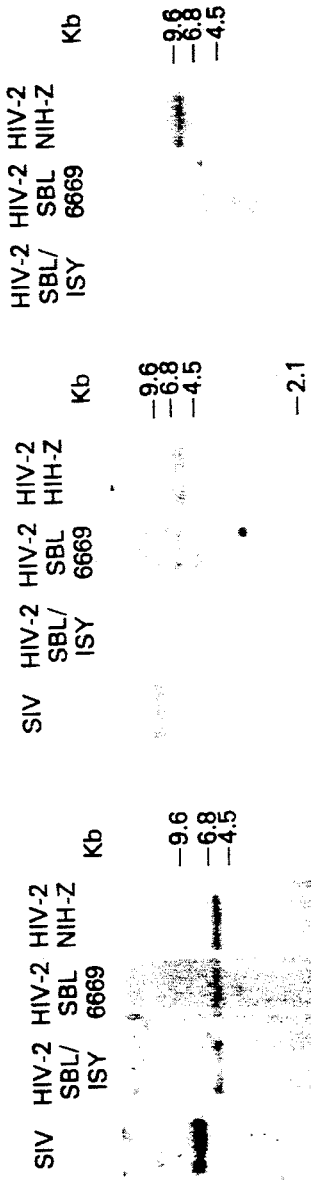

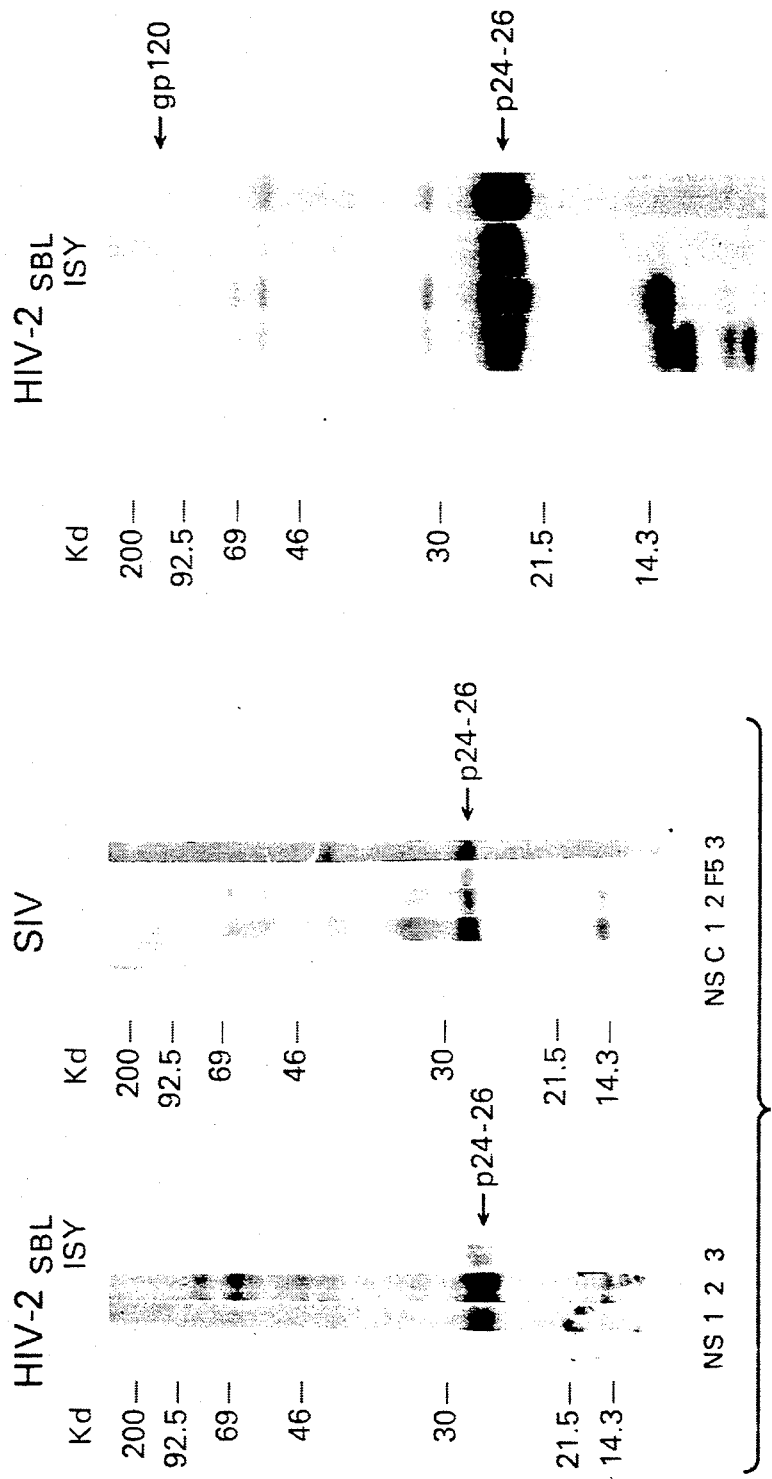

H9 cells

MOLT-3 cells

H9/HIV-2 NIH-Z (8 days)   H9/HIV-2 SBL/ISY (8 days)

Translation of DNA sequence SBLISY.

Total number of bases: 9633.
Translation from base 1 to base 9633.
Done on (absolute) phase(s): 1 , 2 and 3.
Using the Universal genetic code.

```
          10        20        30        40        50        60
           |         |         |         |         |         |
      AGTCGCTCTGCGGAGAGGCTGGCAGATTGAGCCCTGGGAGGTTCTCTCCAGCACTAGCAG

SerArgSerAlaGluArgLeuAlaAsp---AlaLeuGlyGlySerLeuGlnHis---Gln
    ValAlaLeuArgArgGlyTrpGlnIleGluProTrpGluValLeuSerSerThrSerArg
     SerLeuCysGlyGluAlaGlyArgLeuSerProGlyArgPheSerProAlaLeuAlaGly 70        80        90       100       110       120
           |         |         |         |         |         |
      GTAGAGCCTGGGTGTTCCCTGCTGGACTCTCACCAGTGCTTGGCCGGCGCTGGGCAGACG

ValGluProGlyCysSerLeuLeuAspSerHisGlnCysLeuAlaGlyAlaGlyGlnThr
    ---SerLeuGlyValProCysTrpThrLeuThrSerAlaTrpProAlaLeuGlyArgArg
     ArgAlaTrpValPheProAlaGlyLeuSerProValLeuGlyArgArgTrpAlaAspGly 130       140       150       160       170       180
           |         |         |         |         |         |
      GCTCCACGCTTGCTTGCTTAAAAGACCTCTTAATAAAGCTGCCAGTTAGAAGCAAGTTAA

AlaProArgLeuLeuAla---LysThrSer------SerCysGlnLeuGluAlaSer---
    LeuHisAlaCysLeuLeuLysArgProLeuAsnLysAlaAlaSer---LysGlnValLys
     SerThrLeuAlaCysLeuLysAspLeuLeuIleLysLeuProValArgSerLysLeuSer 190       200       210       220       230       240
           |         |         |         |         |         |
      GTGTGTGTTCCCATCTCTCCTAGTCGCCGCCTGGTCATTCGGTGTTCTCCTGAGTAACAA

ValCysValProIleSerProSerArgArgLeuValIleArgCysSerProGlu---Gln
    CysValPheProSerLeuLeuValAlaAlaTrpSerPheGlyValLeuLeuSerAsnLys
     ValCysSerHisLeuSer---SerProProGlyHisSerValPheSer---ValThrArg 250       260       270       280       290       300
           |         |         |         |         |         |
      GACCCTGGTCTGTTAGGACCCTTCTTGCTTTGGGAAACCGAGGCAGGAAAATCCCTAGCA

AspProGlyLeuLeuGlyProPheLeuLeuTrpGluThrGluAlaGlyLysSerLeuAla
    ThrLeuValCys---AspProSerCysPheGlyLysProArgGlnGluAsnPro---Gln
     ProTrpSerValArgThrLeuLeuAlaLeuGlyAsnArgGlyArgLysIleProSerArg
```

FIG. 5b

```
           310       320       330       340       350       360
            |         |         |         |         |         |
     GGTTGGCGCCCGAACAGGGACTTGAGGAAGACTGAGAAGCCTTGGAACACGGCTGAGTGA
```

GlyTrpArgProAsnArgAspLeuArgLysThrGluLysProTrpAsnThrAlaGlu---
ValGlyAlaArgThrGlyThr---GlyArgLeuArgSerLeuGlyThrArgLeuSerGlu
LeuAlaProGluGlnGlyLeuGluGluAsp---GluAlaLeuGluHisGly---ValLys

```
           370       380       390       400       410       420
            |         |         |         |         |         |
     AGGCAGTAAGGGCGGCAGGAACAAACCACGACGGAGTGCTCCTAGAAAGGCGCAGGCCAA
```

ArgGln---GlyArgGlnGluGlnThrThrThrGluCysSer---LysGlyAlaGlyGln
GlySerLysGlyGlyArgAsnLysProArgArgSerAlaProArgLysAlaGlnAlaLys
AlaValArgAlaAlaGlyThrAsnHisAspGlyValLeuLeuGluArgArgArgProArg

```
           430       440       450       460       470       480
            |         |         |         |         |         |
     GGTACCAAAGGCGGCGTGTGGAGCGGGAGTCAAGAGGCCTCCGGGTGAAGGTAAGTACCT
```

GlyThrLysGlyGlyValTrpSerGlySerGlnGluAlaSerGly---Arg---ValPro
ValProLysAlaAlaCysGlyAlaGlyValLysArgProProGlyGluGlyLysTyrLeu
TyrGlnArgArgArgValGluArgGluSerArgGlyLeuArgValLysValSerThrTyr

```
           490       500       510       520       530       540
            |         |         |         |         |         |
     ACACCAAAAACTGTAGCCGGAAAAGGCTTGTTATCCTACCTTTAGACAGGTAGAAGATTG
```

ThrProLysThrValAlaGlyLysGlyLeuLeuSerTyrLeu---ThrGlyArgArgLeu
HisGlnLysLeu---ProGluLysAlaCysTyrProThrPheArgGlnValGluAspCys
ThrLysAsnCysSerArgLysArgLeuValIleLeuProLeuAspArg---LysIleVal

```
           550       560       570       580       590       600
            |         |         |         |         |         |
     TGGGAGATGGGCGCGAAAAACTCCGTCTTGAGAGGGAAAAAGGCAGATGAATTAGAAAAA
```

TrpGluMETGlyAlaLysAsnSerValLeuArgGlyLysLysAlaAspGluLeuGluLys
GlyArgTrpAlaArgLysThrProSer---GluGlyLysArgGlnMETAsn---LysLys
GlyAspGlyArgGluLysLeuArgLeuGluArgGluLysGlyArg---IleArgLysAsn

```
           610       620       630       640       650       660
            |         |         |         |         |         |
     ATTAGGTTACGGCCCGGCGGGAAGAAAAAATACAGATTAAAACATATTGTGTGGGCAGCG
```

IleArgLeuArgProGlyGlyLysLysLysTyrArgLeuLysHisIleValTrpAlaAla
LeuGlyTyrGlyProAlaGlyArgLysAsnThrAsp---AsnIleLeuCysGlyGlnArg
---ValThrAlaArgArgGluGluLysIleGlnIleLysThrTyrCysValGlySerGlu

FIG. 5c

```
          670       680       690       700       710       720
           |         |         |         |         |         |
AATGAATTGGACAGATTCGGATTAACAGAGAGCCTGTTGGAGTCAAAAGAAGGTTGCCAA

AsnGluLeuAspArgPheGlyLeuThrGluSerLeuLeuGluSerLysGluGlyCysGln
METAsnTrpThrAspSerAsp---GlnArgAlaCysTrpSerGlnLysLysValAlaLys
---IleGlyGlnIleArgIleAsnArgGluProValGlyValLysArgArgLeuProLys 730       740       750       760       770       780
           |         |         |         |         |         |
AAAATTATTTCAGTTTTAGAACCATTAGTACCAACAGGGTCAGAAAATTTAAAAAGCCTT

LysIleIleSerValLeuGluProLeuValProThrGlySerGluAsnLeuLysSerLeu
LysLeuPheGlnPhe---AsnHis---TyrGlnGlnGlyGlnLysIle---LysAlaPhe
AsnTyrPheSerPheArgThrIleSerThrAsnArgValArgLysPheLysLysProLeu 790       800       810       820       830       840
           |         |         |         |         |         |
TATAATACTACCTGCGTCATTTGGTGCTTGCACGCAGAAGAGAAAGTGAAAGATACTGAA

TyrAsnThrThrCysValIleTrpCysLeuHisAlaGluGluLysValLysAspThrGlu
IleIleLeuProAlaSerPheGlyAlaCysThrGlnLysArgLys---LysIleLeuLys
---TyrTyrLeuArgHisLeuValLeuAlaArgArgArgGluSerGluArgTyr---Arg 850       860       870       880       890       900
           |         |         |         |         |         |
GAAGCAAAAAGAATAGTAGGGAGACATCTAGTGGCAGAAACAGAAACTGCAGAGAAAATG

GluAlaLysArgIleValGlyArgHisLeuValAlaGluThrGluThrAlaGluLysMET
LysGlnLysGlu------GlyAspIle---TrpGlnLysGlnLysLeuGlnArgLysCys
SerLysLysAsnSerArgGluThrSerSerGlyArgAsnArgAsnCysArgGluAsnAla 910       920       930       940       950       960
           |         |         |         |         |         |
CCAAATATAAGTAGACCAACAGCACCACCTAGCGGGAAAGGGGGAAACTTCCCCGTGCAA

ProAsnIleSerArgProThrAlaProProSerGlyLysGlyGlyAsnPheProValGln
GlnIle---ValAspGlnGlnHisHisLeuAlaGlyLysGlyGluThrSerProCysAsn
LysTyrLys---ThrAsnSerThrThr---ArgGluArgGlyLysLeuProArgAlaThr 970       980       990      1000      1010      1020
           |         |         |         |         |         |
CAAATAGGCGGCAACTATGTCCATCTGCCGCTGAGTCCCCGAACCCTAAATGCTTGGGTA

GlnIleGlyGlyAsnTyrValHisLeuProLeuSerProArgThrLeuAsnAlaTrpVal
Lys---AlaAlaThrMETSerIleCysArg---ValProGluPro---METLeuGly---
AsnArgArgGlnLeuCysProSerAlaAlaGluSerProAsnProLysCysLeuGlyLys 1030      1040      1050      1060      1070      1080
           |         |         |         |         |         |
AAGTTAGTAGAGGAGAAAAAGTTCGGGGCAGAAGTAGTGCCGGGATTTCAGGCACTCTCA

LysLeuValGluGluLysLysPheGlyAlaGluValValProGlyPheGlnAlaLeuSer
Ser------ArgArgLysSerSerGlyGlnLys---CysArgAspPheArgHisSerGln
ValSerArgGlyGluLysValArgGlyArgSerSerAlaGlyIleSerGlyThrLeuArg
```

FIG. 5d

```
         1090      1100      1110      1120      1130      1140
          |         |         |         |         |         |
       GAAGGCTGCACGCCCTATGATATTAATCAAATGCTTAATTGTGTGGGCGACCATCAAGCA

GluGlyCysThrProTyrAspIleAsnGlnMETLeuAsnCysValGlyAspHisGlnAla
       LysAlaAlaArgProMETIleLeuIleLysCysLeuIleValTrpAlaThrIleLysGln
       ArgLeuHisAlaLeu---Tyr---SerAsnAla---LeuCysGlyArgProSerSerSer 1150      1160      1170      1180      1190      1200
          |         |         |         |         |         |
       GCGATGCAAATAATCAGAGAAATTATTAATGAAGAAGCAGCAGACTGGGATGTACAACAT

AlaMETGlnIleIleArgGluIleIleAsnGluGluAlaAlaAspTrpAspValGlnHis
       ArgCysLys---SerGluLysLeuLeuMETLysLysGlnGlnThrGlyMETTyrAsnIle
       AspAlaAsnAsnGlnArgAsnTyr------ArgSerSerArgLeuGlyCysThrThrSer 1210      1220      1230      1240      1250      1260
          |         |         |         |         |         |
       CCAATACCAGGCCCCTTACCAGCGGGGCAGCTCAGAGATCCACGAGGATCTGACATAGCA

ProIleProGlyProLeuProAlaGlyGlnLeuArgAspProArgGlySerAspIleAla
       GlnTyrGlnAlaProTyrGlnArgGlySerSerGluIleHisGluAspLeuThr---Gln
       AsnThrArgProLeuThrSerGlyAlaAlaGlnArgSerThrArgIle---HisSerArg 1270      1280      1290      1300      1310      1320
          |         |         |         |         |         |
       GGGACAACAAGCACAGTAGAGGAACAGATCGAATGGATGTATAGGCAAGAAAATCCTGTA

GlyThrThrSerThrValGluGluGlnIleGluTrpMETTyrArgGlnGluAsnProVal
       GlyGlnGlnAlaGln---ArgAsnArgSerAsnGlyCysIleGlyLysLysIleLeuTyr
       AspAsnLysHisSerArgGlyThrAspArgMETAspVal---AlaArgLysSerCysThr 1330      1340      1350      1360      1370      1380
          |         |         |         |         |         |
       CCAGTAGGAAACATCTATAGGAGATGGATCCAGATAGGACTGCAGAAGTGTGTCAGAATG

ProValGlyAsnIleTyrArgArgTrpIleGlnIleGlyLeuGlnLysCysValArgMET
       Gln---GluThrSerIleGlyAspGlySerArg---AspCysArgSerValSerGluCys
       SerArgLysHisLeu---GluMETAspProAspArgThrAlaGluValCysGlnAsnVal 1390      1400      1410      1420      1430      1440
          |         |         |         |         |         |
       TACAATCCAACCAACATTCTAGACATAAAACAAGGACCAAAAGAGTCGTTCCAAAGCTAT

TyrAsnProThrAsnIleLeuAspIleLysGlnGlyProLysGluSerPheGlnSerTyr
       ThrIleGlnProThrPhe---Thr---AsnLysAspGlnLysSerArgSerLysAlaMET
       GlnSerAsnGlnHisSerArgHisLysThrArgThrLysArgValValProLysLeuCys
```

FIG. 5e

```
       1450      1460      1470      1480      1490      1500
        |         |         |         |         |         |
GTGGATAGATTCTACAAAAGCTTAAGGGCAGAACAGACAGATGCAGCAGTGAAGAATTGG
```

ValAspArgPheTyrLysSerLeuArgAlaGluGlnThrAspAlaAlaValLysAsnTrp
TrpIleAspSerThrLysAla---GlyGlnAsnArgGlnMETGlnGln---ArgIleGly
Gly---IleLeuGlnLysLeuLysGlyArgThrAspArgCysSerSerGluGluLeuAsp

```
       1510      1520      1530      1540      1550      1560
        |         |         |         |         |         |
ATGACCCAGACGCTGCTAGTGCAATCGAACCCAGACTGTAAGTTAGTACTAAAGGGACTA
```

METThrGlnThrLeuLeuValGlnSerAsnProAspCysLysLeuValLeuLysGlyLeu
---ProArgArgCys---CysAsnArgThrGlnThrValSer---Tyr---ArgAsp---
AspProAspAlaAlaSerAlaIleGluProArgLeu---ValSerThrLysGlyThrArg

```
       1570      1580      1590      1600      1610      1620
        |         |         |         |         |         |
GGGATGAATCCTACCTTAGAAGAGATGCTAACCGCCTGTCAAGGGATAGGTGGACCAGGC
```

GlyMETAsnProThrLeuGluGluMETLeuThrAlaCysGlnGlyIleGlyGlyProGly
Gly---IleLeuPro---LysArgCys---ProProValLysGly---ValAspGlnAla
AspGluSerTyrLeuArgArgAspAlaAsnArgLeuSerArgAspArgTrpThrArgPro

```
       1630      1640      1650      1660      1670      1680
        |         |         |         |         |         |
CAGAAGGCCAGACTAATGGCAGAAGCCTTAAAAGAGGCCATGCGACCAGCCCCTATCCCA
```

GlnLysAlaArgLeuMETAlaGluAlaLeuLysGluAlaMETArgProAlaProIlePro
ArgArgProAsp---TrpGlnLysPro---LysArgProCysAspGlnProLeuSerHis
GluGlyGlnThrAsnGlyArgSerLeuLysArgGlyHisAlaThrSerProTyrProIle

```
       1690      1700      1710      1720      1730      1740
        |         |         |         |         |         |
TTTGCAGCAGCCCAACAGAAAAGGGCAATTAAGTGTTGGAATTGTGGAAAGGAAGGGCAC
```

PheAlaAlaAlaGlnGlnLysArgAlaIleLysCysTrpAsnCysGlyLysGluGlyHis
LeuGlnGlnProAsnArgLysGlyGlnLeuSerValGlyIleValGluArgLysGlyThr
CysSerSerProThrGluLysGlyAsn---ValLeuGluLeuTrpLysGlyArgAlaLeu

```
       1750      1760      1770      1780      1790      1800
        |         |         |         |         |         |
TCGGCAAGACAATGCCGAGCGCCTAGAAGACAGGGCTGCTGGAAATGTGGCAAGTCAGGA
```

SerAlaArgGlnCysArgAlaProArgArgGlnGlyCysTrpLysCysGlyLysSerGly
ArgGlnAspAsnAlaGluArgLeuGluAspArgAlaAlaGlyAsnValAlaSerGlnAsp
GlyLysThrMETProSerAla---LysThrGlyLeuLeuGluMETTrpGlnValArgThr

```
       1810      1820      1830      1840      1850      1860
        |         |         |         |         |         |
CACATCATGGCAAACTGCCCAGATAGACAGGCTGGTTTTTTAGGGCTTGGACCATGGGGA
```

HisIleMETAlaAsnCysProAspArgGlnAlaGlyPheLeuGlyLeuGlyProTrpGly
ThrSerTrpGlnThrAlaGlnIleAspArgLeuValPhe---GlyLeuAspHisGlyGlu
HisHisGlyLysLeuProArg---ThrGlyTrpPhePheArgAlaTrpThrMETGlyLys

FIG. 5f

```
          1870      1880      1890      1900      1910      1920
            |         |         |         |         |         |
AAGAAGCCCCGCAACTTCCCCGTGGTCCCAAGTTCGCAGGGGCTAACACCAACAGCACCC

LysLysProArgAsnPheProValValProSerSerGlnGlyLeuThrProThrAlaPro
 ArgSerProAlaThrSerProTrpSerGlnValArgArgGly---HisGlnGlnHisPro
 GluAlaProGlnLeuProArgGlyProLysPheAlaGlyAlaAsnThrAsnSerThrPro 1930      1940      1950      1960      1970      1980
            |         |         |         |         |         |
CCAATGGATCCAGCAGTGGACCTACTGGAGAAGTACATGCAGCAAGGGAGAAAACAGAGA

ProMETAspProAlaValAspLeuLeuGluLysTyrMETGlnGlnGlyArgLysGlnArg
 GlnTrpIleGlnGlnTrpThrTyrTrpArgSerThrCysSerLysGlyGluAsnArgGlu
 AsnGlySerSerSerGlyProThrGlyGluValHisAlaAlaArgGluLysThrGluArg 1990      2000      2010      2020      2030      2040
            |         |         |         |         |         |
GAGCAGAGACAAAGACCATACAAAGAAGTGACAGAGGACTTGCTGCATCTCGAGCAAGGA

GluGlnArgGlnArgProTyrLysGluValThrGluAspLeuLeuHisLeuGluGlnGly
 SerArgAspLysAspHisThrLysLys---GlnArgThrCysCysIleSerSerLysGlu
 AlaGluThrLysThrIleGlnArgSerAspArgGlyLeuAlaAlaSerArgAlaArgArg 2050      2060      2070      2080      2090      2100
            |         |         |         |         |         |
GAGACACCACACAGAGAGACGACAGAGGACTTGCTGCACCTCAATTCTCTCTTTGGAAAC

GluThrProHisArgGluThrThrGluAspLeuLeuHisLeuAsnSerLeuPheGlyAsn
 ArgHisHisThrGluArgArgGlnArgThrCysCysThrSerIleLeuSerLeuGluThr
 AspThrThrGlnArgAspAspArgGlyLeuAlaAlaProGlnPheSerLeuTrpLysArg 2110      2120      2130      2140      2150      2160
            |         |         |         |         |         |
GACCAGTAGTCACAGCATACATTGAGGATCAGCCAGTAGAAGTTTTACTAGACACAGGGG

AspGln---SerGlnHisThrLeuArgIleSerGln---LysPheTyr---ThrGlnGly
 ThrSerSerHisSerIleHis---GlySerAlaSerArgSerPheThrArgHisArgGly
 ProValValThrAlaTyrIleGluAspGlnProValGluValLeuLeuAspThrGlyAla 2170      2180      2190      2200      2210      2220
            |         |         |         |         |         |
CTGACGACTCAATAGTAGCAGGAATAGAGTTAGGGAGCAATTATAGTCCAAAAATAGTAG

LeuThrThrGln------GlnGlu---Ser---GlyAlaIleIleValGlnLys------
 ---ArgLeuAsnSerSerArgAsnArgValArgGluGlnLeu---SerLysAsnSerArg
 AspAspSerIleValAlaGlyIleGluLeuGlySerAsnTyrSerProLysIleValGly 2230      2240      2250      2260      2270      2280
            |         |         |         |         |         |
GGGGAATAGGAGGATTCATAAATACCAAAGAATATAAAGATGTAGAAATAAGAGTGCTAA

GlyGlu---GluAspSer---IleProLysAsnIleLysMET---Lys---GluCys---
 GlyAsnArgArgIleHisLysTyrGlnArgIle---ArgCysArgAsnLysSerAlaLys
 GlyIleGlyGlyPheIleAsnThrLysGluTyrLysAspValGluIleArgValLeuAsn
```

FIG. 5g

```
            2290      2300      2310      2320      2330      2340
              |         |         |         |         |         |
ATAAAAAGGTAAGAGCCACCATAATGACAGGTGATACCCCAATCAACATTTTTGGCAGAA

IleLysArg---GluProPro------GlnValIleProGlnSerThrPheLeuAlaGlu
---LysGlyLysSerHisHisAsnAspArg---TyrProAsnGlnHisPheTrpGlnLys
LysLysValArgAlaThrIleMETThrGlyAspThrProIleAsnIlePheGlyArgAsn 2350      2360      2370      2380      2390      2400
              |         |         |         |         |         |
ATATCCTGACAGCCTTGGGCATGTCATTAAATTTACCAGTCGCCAAAATAGAACCAGTAA

IleSer---GlnProTrpAlaCysHis---IleTyrGlnSerProLys---AsnGln---
TyrProAspSerLeuGlyHisValIleLysPheThrSerArgGlnAsnArgThrSerLys
IleLeuThrAlaLeuGlyMETSerLeuAsnLeuProValAlaLysIleGluProValLys 2410      2420      2430      2440      2450      2460
              |         |         |         |         |         |
AAGTAACATTAAAGCCAGGAAAAGATGGGCCAAAACAAAGACAATGGCCCTTAACAAGAG

Lys---His---SerGlnGluLysMETGlyGlnAsnLysAspAsnGlyPro---GlnGlu
SerAsnIleLysAlaArgLysArgTrpAlaLysThrLysThrMETAlaLeuAsnLysArg
ValThrLeuLysProGlyLysAspGlyProLysGlnArgGlnTrpProLeuThrArgGlu 2470      2480      2490      2500      2510      2520
              |         |         |         |         |         |
AAAAAATAGAAGCACTAAGAGAAATCTGTGAAAAAATGGAAAGAGAAGGTCAGCTAGAAG

LysLys---LysHis---GluLysSerValLysLysTrpLysGluLysValSer---Lys
LysAsnArgSerThrLysArgAsnLeu---LysAsnGlyLysArgArgSerAlaArgArg
LysIleGluAlaLeuArgGluIleCysGluLysMETGluArgGluGlyGlnLeuGluGlu 2530      2540      2550      2560      2570      2580
              |         |         |         |         |         |
AAGCGCCTCCAACTAATCCCTATAATACCCCTACATTTGCAATTAAGAAAAAGGACAAAA

LysArgLeuGlnLeuIleProIleIleProLeuHisLeuGlnLeuArgLysArgThrLys
SerAlaSerAsn---SerLeu---TyrProTyrIleCysAsn---GluLysGlyGlnLys
AlaProProThrAsnProTyrAsnThrProThrPheAlaIleLysLysLysAspLysAsn 2590      2600      2610      2620      2630      2640
              |         |         |         |         |         |
ACAAATGGAGGATGCTGATAGATTTTAGAGAACTAAACAAGGTAACTCAAGATTTCACAG

ThrAsnGlyGlyCys------IleLeuGluAsn---ThrArg---LeuLysIleSerGln
GlnMETGluAspAlaAspArgPhe---ArgThrLysGlnGlyAsnSerArgPheHisArg
LysTrpArgMETLeuIleAspPheArgGluLeuAsnLysValThrGlnAspPheThrGlu
```

FIG. 5h

```
         2650      2660      2670      2680      2690      2700
          |         |         |         |         |         |
AGGTTCAGTTAGGAATTCCACACCCAGCAGGATTAGCCAAGAAAAGAAGAATTACTGTGT
```

ArgPheSer---GluPheHisThrGlnGlnAsp---ProArgLysGluGluLeuLeuCys
GlySerValArgAsnSerThrProSerArgIleSerGlnGluLysLysAsnTyrCysVal
ValGlnLeuGlyIleProHisProAlaGlyLeuAlaLysLysArgArgIleThrValLeu

```
         2710      2720      2730      2740      2750      2760
          |         |         |         |         |         |
TAGATGTAGGAGATGCCTACTTTTCCATACCCCTATATGAGGATTTTAGACAGTATACTG
```

---MET---GluMETProThrPheProTyrProTyrMETArgIleLeuAspSerIleLeu
ArgCysArgArgCysLeuLeuPheHisThrProIle---GlyPhe---ThrValTyrCys
AspValGlyAspAlaTyrPheSerIleProLeuTyrGluAspPheArgGlnTyrThrAla

```
         2770      2780      2790      2800      2810      2820
          |         |         |         |         |         |
CATTTACTCTGCCATCAGTAAACAATGCAGAACCAGGAAAAAGATATATATACAAAGTCT
```

HisLeuLeuCysHisGln---ThrMETGlnAsnGlnGluLysAspIleTyrThrLysSer
IleTyrSerAlaIleSerLysGlnCysArgThrArgLysLysIleTyrIleGlnSerLeu
PheThrLeuProSerValAsnAsnAlaGluProGlyLysArgTyrIleTyrLysValLeu

```
         2830      2840      2850      2860      2870      2880
          |         |         |         |         |         |
TACCACAGGGATGGAAGGGGTCACCAGCAATTTTTCAATACACAATGAGGCAAGTCTTAG
```

TyrHisArgAspGlyArgGlyHisGlnGlnPhePheAsnThrGln---GlyLysSer---
ThrThrGlyMETGluGlyValThrSerAsnPheSerIleHisAsnGluAlaSerLeuArg
ProGlnGlyTrpLysGlySerProAlaIlePheGlnTyrThrMETArgGlnValLeuGlu

```
         2890      2900      2910      2920      2930      2940
          |         |         |         |         |         |
AACCATTCAGAAAAGCAAACCCAGATGTCATTATCGTTCAGTACATGGATGATATCTTAA
```

AsnHisSerGluLysGlnThrGlnMETSerLeuSerPheSerThrTrpMETIleSer---
ThrIleGlnLysSerLysProArgCysHisTyrArgSerValHisGly---TyrLeuAsn
ProPheArgLysAlaAsnProAspValIleIleValGlnTyrMETAspAspIleLeuIle

```
         2950      2960      2970      2980      2990      3000
          |         |         |         |         |         |
TAGCTAGTGACAGGACAGATTTGGAACATGACAAAGTAGTCCTACAGCTAAAGGAACTTC
```

---LeuValThrGlyGlnIleTrpAsnMETThrLys---SerTyrSer---ArgAsnPhe
Ser------GlnAspArgPheGlyThr---GlnSerSerProThrAlaLysGlyThrSer
AlaSerAspArgThrAspLeuGluHisAspLysValValLeuGlnLeuLysGluLeuLeu

FIG. 5i

```
           3010      3020      3030      3040      3050      3060
             |         |         |         |         |         |
       TAAATGGCCTGGGATTTTCCACCCCAGACGAAAAGTTCCAAAAGGACCCTCCATACCAAT

---METAlaTrpAspPheProProGlnThrLysSerSerLysArgThrLeuHisThrAsn
       LysTrpProGlyIlePheHisProArgArgLysValProLysGlyProSerIleProMET
       AsnGlyLeuGlyPheSerThrProAspGluLysPheGlnLysAspProProTyrGlnTrp 3070      3080      3090      3100      3110      3120
             |         |         |         |         |         |
       GGATGGGCTATGAACTGTGGCCAACCAAATGGAAATTGCAAAAAATACAATTGCCCCAAA

GlyTrpAlaMETAsnCysGlyGlnProAsnGlyAsnCysLysLysTyrAsnCysProLys
       AspGlyLeu---ThrValAlaAsnGlnMETGluIleAlaLysAsnThrIleAlaProLys
       METGlyTyrGluLeuTrpProThrLysTrpLysLeuGlnLysIleGlnLeuProGlnLys 3130      3140      3150      3160      3170      3180
             |         |         |         |         |         |
       AGGAAGTATGGACAGTTAATGACATCCAGAAACTAGTGGGTGTCCTAAACTGGGCGGCAC

ArgLysTyrGlyGlnLeuMETThrSerArgAsn---TrpValSer---ThrGlyArgHis
       GlySerMETAspSer------HisProGluThrSerGlyCysProLysLeuGlyGlyThr
       GluValTrpThrValAsnAspIleGlnLysLeuValGlyValLeuAsnTrpAlaAlaGln 3190      3200      3210      3220      3230      3240
             |         |         |         |         |         |
       AAATCTACCCAGGAATAAAGACCAAACACTTATGTAAGCTAATTAGAGGAAAGATGACAC

LysSerThrGlnGlu---ArgProAsnThrTyrValSer---LeuGluGluArg---His
       AsnLeuProArgAsnLysAspGlnThrLeuMET---AlaAsn---ArgLysAspAspThr
       IleTyrProGlyIleLysThrLysHisLeuCysLysLeuIleArgGlyLysMETThrPro 3250      3260      3270      3280      3290      3300
             |         |         |         |         |         |
       CCACGGAAGAAGTACAGTGGACAGAATTAGCAGAAGCAGAGCTGGAGGAAAACAAAATTA

ProArgLysLysTyrSerGlyGlnAsn---GlnLysGlnSerTrpArgLysThrLysLeu
       HisGlyArgSerThrValAspArgIleSerArgSerArgAlaGlyGlyLysGlnAsnTyr
       ThrGluGluValGlnTrpThrGluLeuAlaGluAlaGluLeuGluAsnLysIleIle 3310      3320      3330      3340      3350      3360
             |         |         |         |         |         |
       TCTTAAGCCAGGAACAGGAGGGACACTATTACCAAGAGGAAAAAGAGTTAGAAGCAACAG

Ser---AlaArgAsnArgArgAspThrIleThrLysArgLysLysSer---LysGlnGln
       LeuLysProGlyThrGlyGlyThrLeuLeuProArgGlyLysArgValArgSerAsnSer
       LeuSerGlnGluGlnGluGlyHisTyrTyrGlnGluGluLysGluLeuGluAlaThrVal
```

FIG. 5j

```
          3370      3380      3390      3400      3410      3420
            |         |         |         |         |         |
TTCAAAAGGATCAAGACAATCAGTGGACATATAAAGTACACCAGGGAGAAAAAATTCTAA

PheLysArgIleLysThrIleSerGlyHisIleLysTyrThrArgGluLysLysPhe---
 SerLysGlySerArgGlnSerValAspIle---SerThrProGlyArgLysAsnSerLys
  GlnLysAspGlnAspAsnGlnTrpThrTyrLysValHisGlnGlyGluLysIleLeuLys 3430      3440      3450      3460      3470      3480
            |         |         |         |         |         |
AAGTAGGAAAATATGCAAAGATAAAAAATACCCATACCAACGGGGTCAGGTTGTTGGCAC

Lys---GluAsnMETGlnArg---LysIleProIleProThrGlySerGlyCysTrpHis
 SerArgLysIleCysLysAspLysLysTyrProTyrGlnArgGlyGlnValValGlyThr
  ValGlyLysTyrAlaLysIleLysAsnThrHisThrAsnGlyValArgLeuLeuAlaGln 3490      3500      3510      3520      3530      3540
            |         |         |         |         |         |
AGGTAGTTCAGAAAATAGGAAAAGAAGCACTAGTCATTTGGGGACGAATACCAAAATTTC

Arg---PheArgLys---GluLysLysHis---SerPheGlyAspGluTyrGlnAsnPhe
 GlySerSerGluAsnArgLysArgSerThrSerHisLeuGlyThrAsnThrLysIleSer
  ValValGlnLysIleGlyLysGluAlaLeuValIleTrpGlyArgIleProLysPheHis 3550      3560      3570      3580      3590      3600
            |         |         |         |         |         |
ACCTACCAGTAGAAAGAGAGACCTGGGAACAGTGGTGGGATAACTATTGGCAAGTGACAT

ThrTyrGln---LysGluArgProGlyAsnSerGlyGlyIleThrIleGlyLys---His
 ProThrSerArgLysArgAspLeuGlyThrValValGly---LeuLeuAlaSerAspMET
  LeuProValGluArgGluThrTrpGluGlnTrpTrpAspAsnTyrTrpGlnValThrTrp 3610      3620      3630      3640      3650      3660
            |         |         |         |         |         |
GGATCCCAGACTGGGACTTCGTATCCACCCCACCGTTGGTCAGGTTAGCATTTAACCTGG

GlySerGlnThrGlyThrSerTyrProProHisArgTrpSerGly---HisLeuThrTrp
 AspProArgLeuGlyLeuArgIleHisProThrValGlyGlnValSerIle---ProGly
  IleProAspTrpAspPheValSerThrProProLeuValArgLeuAlaPheAsnLeuVal 3670      3680      3690      3700      3710      3720
            |         |         |         |         |         |
TAAAAGATCCTATACCAGGCGCAGAGACCTTCTACACGGATGGATCTTGCAATAGGCAAT

---LysIleLeuTyrGlnAlaGlnArgProSerThrArgMETAspLeuAlaIleGlyAsn
 LysArgSerTyrThrArgArgArgAspLeuLeuHisGlyTrpIleLeuGln---AlaIle
  LysAspProIleProGlyAlaGluThrPheTyrThrAspGlySerCysAsnArgGlnSer
```

FIG. 5k

```
          3730      3740      3750      3760      3770      3780
            |         |         |         |         |         |
        CAAAAGAGGGAAAAGCAGGATATATAACAGATAGAGGAAAAGACAAAGTAAGGATATTAG

GlnLysArgGluLysGlnAspIle---GlnIleGluGluLysThrLys---GlyTyr---
        LysArgGlyLysSerArgIleTyrAsnArg---ArgLysArgGlnSerLysAspIleArg
        LysGluGlyLysAlaGlyTyrIleThrAspArgGlyLysAspLysValArgIleLeuGlu 3790      3800      3810      3820      3830      3840
            |         |         |         |         |         |
        AGCAAACTACCAACCAACAAGCAGAATTAGAAGCCTTTGCAATGGCAGTAACAGACTCAG

SerLysLeuProThrAsnLysGlnAsn---LysProLeuGlnTrpGln---GlnThrGln
        AlaAsnTyrGlnProThrSerArgIleArgSerLeuCysAsnGlySerAsnArgLeuArg
        GlnThrThrAsnGlnGlnAlaGluLeuGluAlaPheAlaMETAlaValThrAspSerGly 3850      3860      3870      3880      3890      3900
            |         |         |         |         |         |
        GTCCAAAAGTCAATATTGTAGTAGACTCACAGTATGTAATGGGAATAGTAACAGGCCAAC

ValGlnLysSerIleLeu------ThrHisSerMET---TrpGlu------GlnAlaAsn
        SerLysSerGlnTyrCysSerArgLeuThrValCysAsnGlyAsnSerAsnArgProThr
        ProLysValAsnIleValValAspSerGlnTyrValMETGlyIleValThrGlyGlnPro 3910      3920      3930      3940      3950      3960
            |         |         |         |         |         |
        CGGCTGAATCAGAGAGTAGAATAGTAAATAAAATTATAGAAGAGATGATAAAAAAGGAAG

ArgLeuAsnGlnArgValGlu------IleLysLeu---LysArg------LysArgLys
        Gly---IleArgGlu---AsnSerLys---AsnTyrArgArgAspAspLysLysGlySer
        AlaGluSerGluSerArgIleValAsnLysIleIleGluGluMETIleLysLysGluAla 3970      3980      3990      4000      4010      4020
            |         |         |         |         |         |
        CAATCTATGTTGCATGGGTCCCGGCCCACAAAGGCATAGGAGGAAATCAAGAAATTGACC

GlnSerMETLeuHisGlySerArgProThrLysAla---GluGluIleLysLysLeuThr
        AsnLeuCysCysMETGlyProGlyProGlnArgHisArgArgLysSerArgAsn---Pro
        IleTyrValAlaTrpValProAlaHisLysGlyIleGlyGlyAsnGlnGluIleAspHis 4030      4040      4050      4060      4070      4080
            |         |         |         |         |         |
        ACTTAGTAAGTCAGGGCATCAGACAAGTATTATTCCTAGAGAGAATAGAGCCCGCTCAGG

Thr------ValArgAlaSerAspLysTyrTyrSer---ArgGlu---SerProLeuArg
        LeuSerLysSerGlyHisGlnThrSerIleIleProArgGluAsnArgAlaArgSerGly
        LeuValSerGlnGlyIleArgGlnValLeuPheLeuGluArgIleGluProAlaGlnGlu
```

FIG. 51

```
         4090      4100      4110      4120      4130      4140
          |         |         |         |         |         |
AAGAACATGGAAAATATCATAGCAATGTAAAAGAACTAGCCCATAAGTTTGGATTACCCA

LysAsnMETGluAsnIleIleAlaMET---LysAsn---ProIleSerLeuAspTyrPro
ArgThrTrpLysIleSer---GlnCysLysArgThrSerPro---ValTrpIleThrGln
GluHisGlyLysTyrHisSerAsnValLysGluLeuAlaHisLysPheGlyLeuProAsn 4150      4160      4170      4180      4190      4200
          |         |         |         |         |         |
ACCTGGTGGCAAGACAAATAGTAAACACATGTGCCCAGTGCCAACAAAAAGGGGAAGCTA

ThrTrpTrpGlnAspLys------ThrHisValProSerAlaAsnLysLysGlyLysLeu
ProGlyGlyLysThrAsnSerLysHisMETCysProValProThrLysArgGlySerTyr
LeuValAlaArgGlnIleValAsnThrCysAlaGlnCysGlnGlnLysGlyGluAlaIle 4210      4220      4230      4240      4250      4260
          |         |         |         |         |         |
TACATGGGCAAGTAAATGCAGAACTAGGCACCTGGCAAATGGACTGCACACACTTAGAAG

TyrMETGlyLys---METGlnAsn---AlaProGlyLysTrpThrAlaHisThr---Lys
ThrTrpAlaSerLysCysArgThrArgHisLeuAlaAsnGlyLeuHisThrLeuArgArg
HisGlyGlnValAsnAlaGluLeuGlyThrTrpGlnMETAspCysThrHisLeuGluGly 4270      4280      4290      4300      4310      4320
          |         |         |         |         |         |
GAAAAATCATTATAGTAGCAGTACATGTTGCAAGTGGATTTATAGAAGCAGAAGTCATCC

GluLysSerLeu------GlnTyrMETLeuGlnValAspLeu---LysGlnLysSerSer
LysAsnHisTyrSerSerSerThrCysCysLysTrpIleTyrArgSerArgSerHisPro
LysIleIleIleValAlaValHisValAlaSerGlyPheIleGluAlaGluValIlePro 4330      4340      4350      4360      4370      4380
          |         |         |         |         |         |
CACAGGAATCAGGAAGGCAAACAGCACTCTTCCTATTAAAACTGGCCAGTAGGTGGCCAA

HisArgAsnGlnGluGlyLysGlnHisSerSerTyr---AsnTrpProValGlyGlyGln
ThrGlyIleArgLysAlaAsnSerThrLeuProIleLysThrGlyGln---ValAlaAsn
GlnGluSerGlyArgGlnThrAlaLeuPheLeuLeuLysLeuAlaSerArgTrpProIle 4390      4400      4410      4420      4430      4440
          |         |         |         |         |         |
TAACACACTTGCACACAGATAATGGTGCCAACTTCACTTCACAGGAGGTAAAGATGGTAG

---HisThrCysThrGlnIleMETValProThrSerLeuHisArgArg---ArgTrp---
AsnThrLeuAlaHisArg---TrpCysGlnLeuHisPheThrGlyGlyLysAspGlySer
ThrHisLeuHisThrAspAsnGlyAlaAsnPheThrSerGlnGluValLysMETValAla
```

FIG. 5m

```
         4450      4460      4470      4480      4490      4500
          |         |         |         |         |         |
CATGGTGGGTAGGCATAGAACAATCCTTTGGAGTACCTTACAATCCACAAAGCCAGGGAG
```

HisGlyGly---Ala---AsnAsnProLeuGluTyrLeuThrIleHisLysAlaArgGlu
METValGlyArgHisArgThrIleLeuTrpSerThrLeuGlnSerThrLysProGlySer
TrpTrpValGlyIleGluGlnSerPheGlyValProTyrAsnProGlnSerGlnGlyVal

```
         4510      4520      4530      4540      4550      4560
          |         |         |         |         |         |
TAGTAGAAGCAATGAATCACCACCTGAAAAATCAGATAGAAAGAATTAGAGAGCAGGCAA
```

------LysGln---IleThrThr---LysIleArg---LysGluLeuGluSerArgGln
SerArgSerAsnGluSerProProGluLysSerAspArgLysAsn---ArgAlaGlyLys
ValGluAlaMETAsnHisHisLeuLysAsnGlnIleGluArgIleArgGluGlnAlaAsn

```
         4570      4580      4590      4600      4610      4620
          |         |         |         |         |         |
ATACAATGGAAACAATAGTACTAATGGCAGTTCATTGCATGAATTTTAAAAGAAGGGGAG
```

IleGlnTrpLysGln---Tyr---TrpGlnPheIleAla---IleLeuLysGluGlyGlu
TyrAsnGlyAsnAsnSerThrAsnGlySerSerLeuHisGluPhe---LysLysGlyArg
ThrMETGluThrIleValLeuMETAlaValHisCysMETAsnPheLysArgArgGlyGly

```
         4630      4640      4650      4660      4670      4680
          |         |         |         |         |         |
GAATAGGGGATATGACCCCAGTAGAAAGACTAGTCAATATGATCACCACAGAACAAGAAA
```

Glu---GlyIle---ProGln---LysAsp---SerIle---SerProGlnAsnLysLys
AsnArgGlyTyrAspProSerArgLysThrSerGlnTyrAspHisHisArgThrArgAsn
IleGlyAspMETThrProValGluArgLeuValAsnMETIleThrThrGluGlnGluIle

```
         4690      4700      4710      4720      4730      4740
          |         |         |         |         |         |
TACAATTCCTCCAAGCAAAAAATTCAAAATTAAAAAAATTTTCGGGTCTATTTCAGAGAAG
```

TyrAsnSerSerLysGlnLysIleGlnAsn---LysIlePheGlySerIleSerGluLys
ThrIleProProSerLysLysPheLysIleLysLysPheSerGlyLeuPheGlnArgArg
GlnPheLeuGlnAlaLysAsnSerLysLeuLysAsnPheArgValTyrPheArgGluGly

```
         4750      4760      4770      4780      4790      4800
          |         |         |         |         |         |
GCAGAAATCAACTGTGGCAAGGACCTGGGGAGCTACTGTGGAAAGGGGACGGAGCAGTCA
```

AlaGluIleAsnCysGlyLysAspLeuGlySerTyrCysGlyLysGlyThrGluGlnSer
GlnLysSerThrValAlaArgThrTrpGlyAlaThrValGluArgGlyArgSerSerHis
ArgAsnGlnLeuTrpGlnGlyProGlyGluLeuLeuTrpLysGlyAspGlyAlaValIle

FIG. 5n

```
        4810      4820      4830      4840      4850      4860
         |         |         |         |         |         |
TAGTCAAGGTAGGGACAGATATAAAAGTAATACCAAGAAGAAAGGCCAAGATCATCAGAG

---SerArg---GlyGlnIle---Lys---TyrGlnGluGluArgProArgSerSerGlu
  SerGlnGlyArgAspArgTyrLysSerAsnThrLysLysLysGlyGlnAspHisGlnArg
   ValLysValGlyThrAspIleLysValIleProArgArgLysAlaLysIleIleArgAsp 4870      4880      4890      4900      4910      4920
         |         |         |         |         |         |
ACTATGGACCAAGGCAAGAGATGGATAGCGGTTCCCACCTGGAGGGTGCCAGGGAGGATG

ThrMETAspGlnGlyLysArgTrpIleAlaValProThrTrpArgValProGlyArgMET
 LeuTrpThrLysAlaArgAspGly---ArgPheProProGlyGlyCysGlnGlyGlyTrp
  TyrGlyProArgGlnGluMETAspSerGlySerHisLeuGluGlyAlaArgGluAspGly 4930      4940      4950      4960      4970      4980
         |         |         |         |         |         |
GAGAAATGGCATAGCCTTATCAAGTATCTAAAATACAGAACAAAAGATCTAGAACAGGTG

GluLysTrpHisSerLeuIleLysTyrLeuLysTyrArgThrLysAspLeuGluGlnVal
 ArgAsnGlyIleAlaLeuSerSerIle---AsnThrGluGlnLysIle---AsnArgCys
  GluMETAla---ProTyrGlnValSerLysIleGlnAsnLysArgSerArgThrGlyAla 4990      5000      5010      5020      5030      5040
         |         |         |         |         |         |
CGCTATGTTCCCCACCATAAGGTGGGGTGGGCATGGTGGACTTGCAGCAGGGTAATATTC

ArgTyrValProHisHisLysValGlyTrpAlaTrpTrpThrCysSerArgValIlePhe
 AlaMETPheProThrIleArgTrpGlyGlyHisGlyGlyLeuAlaAlaGly---TyrSer
  LeuCysSerProPro---GlyGlyValGlyMETValAspLeuGlnGlnGlyAsnIlePro 5050      5060      5070      5080      5090      5100
         |         |         |         |         |         |
CCATTAAAAGGAAACAGTCATCTAGAGATACAGGCATATTGGAACCTAACACCAGAAAAA

ProLeuLysGlyAsnSerHisLeuGluIleGlnAlaTyrTrpAsnLeuThrProGluLys
 His---LysGluThrValIle---ArgTyrArgHisIleGlyThr---HisGlnLysLys
  IleLysArgLysGlnSerSerArgAspThrGlyIleLeuGluProAsnThrArgLysArg 5110      5120      5130      5140      5150      5160
         |         |         |         |         |         |
GGATGGCTCTCCTCTTATTCAGTAAGAATGACTTGGTACTCAGAAGGGGTTCTGGACAGAT

GlyTrpLeuSerSerTyrSerValArgMETThrTrpTyrSerGluGlyPheTrpThrAsp
 AspGlySerProLeuIleGln---Glu---LeuGlyThrGlnLysGlySerGlyGlnMET
  METAlaLeuLeuLeuPheSerLysAsnAspLeuValLeuArgArgValLeuAspArgCys
```

FIG. 5o

```
              5170      5180      5190      5200      5210      5220
                |         |         |         |         |         |
      GTTACCCCAGACTGTGCAGACACCCTAATACACAGCACTTATTTCTCTTGCTTTACGGCA

ValThrProAspCysAlaAspThrLeuIleHisSerThrTyrPheSerCysPheThrAla
 LeuProGlnThrValGlnThrPro---TyrThrAlaLeuIleSerLeuAlaLeuArgGln
  TyrProArgLeuCysArgHisProAsnThrGlnHisLeuPheLeuLeuLeuTyrGlyArg 5230      5240      5250      5260      5270      5280
                |         |         |         |         |         |
      GGTGAAGTAAGAAGAGCCATCAGGGGAGAAAAGTCATTGTCCTGCTGCAATTATCCCCAA

GlyGluValArgArgAlaIleArgGlyGluLysSerLeuSerCysCysAsnTyrProGln
 ValLys---GluGluProSerGlyGluLysSerHisCysProAlaAlaIleIleProLys
  ---SerLysLysSerHisGlnGlyArgLysValIleValLeuLeuGlnLeuSerProSer 5290      5300      5310      5320      5330      5340
                |         |         |         |         |         |
      GCCCATAAGTCCAAGGTACCGTCACTCCAATTTCTGGCCTTAGTAGTAGTACAGCAAAAT

AlaHisLysSerLysValProSerLeuGlnPheLeuAlaLeuValValValGlnGlnAsn
 ProIleSerProArgTyrArgHisSerAsnPheTrpPro---------TyrSerLysMET
  Pro---ValGlnGlyThrValThrProIleSerGlyLeuSerSerSerThrAlaLys---

5350      5360      5370      5380      5390      5400
                |         |         |         |         |         |
      GACAAACCCCAGAGAGACAATACCACCAGGAAACAGTGGCGAAGAAACTATCGAAGAGGC

AspLysProGlnArgAspAsnThrThrArgLysGlnTrpArgArgAsnTyrArgArgGly
 ThrAsnProArgGluThrIleProProGlyAsnSerGlyGluGluThrIleGluGluAla
  GlnThrProGluArgGlnTyrHisGlnGluThrValAlaLysLysLeuSerLysArgPro 5410      5420      5430      5440      5450      5460
                |         |         |         |         |         |
      CTTCGATTGGCTAGACAGGACGGTAGAAGCCATAAACAGAGAGGCAGTGAACCACCTGCC

LeuArgLeuAlaArgGlnAspGlyArgSerHisLysGlnArgGlySerGluProProAla
 PheAspTrpLeuAspArgThrValGluAlaIleAsnArgGluAlaValAsnHisLeuPro
  SerIleGly---ThrGlyArg---LysPro---ThrGluArgGln---ThrThrCysPro 5470      5480      5490      5500      5510      5520
                |         |         |         |         |         |
      CAGGGAGCTTATTTTCCAGGTGTGGCAAAGGTCCTGGAGATACTGGCATGATGAGCAAGG

GlnGlyAlaTyrPheProGlyValAlaLysValLeuGluIleLeuAla------AlaArg
 ArgGluLeuIlePheGlnValTrpGlnArgSerTrpArgTyrTrpHisAspGluGlnGly
  GlySerLeuPheSerArgCysGlyLysGlyProGlyAspThrGlyMETMETSerLysGly
```

FIG. 5p

```
            5530       5540       5550       5560       5570       5580
             |          |          |          |          |          |
    GATGTCACGAAGCTACACAAAGTATAGATATTTGTGCTTAATGCAGAAAGCTGTGTTCAT

AspValThrLysLeuHisLysVal---IlePheValLeuAsnAlaGluSerCysValHis
METSerArgSerTyrThrLysTyrArgTyrLeuCysLeuMETGlnLysAlaValPheMET
CysHisGluAlaThrGlnSerIleAspIleCysAla---CysArgLysLeuCysSerCys 5590       5600       5610       5620       5630       5640
             |          |          |          |          |          |
    GCATTTCAAGAAAGGGTGCACTTGCCGGGGGGAAGGACATGGGCCAGGAGGGTGGAGATC

AlaPheGlnGluArgValHisLeuProGlyGlyArgThrTrpAlaArgArgValGluIle
HisPheLysLysGlyCysThrCysArgGlyGluGlyHisGlyProGlyGlyTrpArgSer
IleSerArgLysGlyAlaLeuAlaGlyGlyLysAspMETGlyGlnGluGlyGlyAspGln 5650       5660       5670       5680       5690       5700
             |          |          |          |          |          |
    AGGACCTCCCCCTCCTCCTCCCCCAGGTTTAGTCTAATGACTGAAGCACCAGCAGAGTTT

ArgThrSerProSerSerSerProArgPheSerLeuMETThrGluAlaProAlaGluPhe
GlyProProProProProProProGlyLeuVal------LeuLysHisGlnGlnSerPhe
AspLeuProLeuLeuLeuProGlnVal---SerAsnAsp---SerThrSerArgValSer 5710       5720       5730       5740       5750       5760
             |          |          |          |          |          |
    CCCCCGGAGGATGGGACCCCCACCGAGGGAACCAGGGGATGAGTGGGTAATAGAAATTCTG

ProProGluAspGlyThrProProArgGluProGlyAspGluTrpValIleGluIleLeu
ProArgArgMETGlyProHisArgGlyAsnGlnGlyMETSerGly------LysPhe---
ProGlyGlyTrpAspProThrGluGlyThrArgGly---ValGlyAsnArgAsnSerGlu 5770       5780       5790       5800       5810       5820
             |          |          |          |          |          |
    AGAGAAATAAAGGAAGAAGCTTTAAAGCATTTTGACCCTCGCTTGCTAACTGCTCTTGGC

ArgGluIleLysGluGluAlaLeuLysHisPheAspProArgLeuLeuThrAlaLeuGly
GluLys---ArgLysLysLeu---SerIleLeuThrLeuAlaCys---LeuLeuLeuAla
ArgAsnLysGlyArgSerPheLysAlaPhe---ProSerLeuAlaAsnCysSerTrpLeu 5830       5840       5850       5860       5870       5880
             |          |          |          |          |          |
    TACTATATCTATACTAGACATGGAGACACCGTTGAAGGCGCCAGAGAGCTCATTAGGGTC

TyrTyrIleTyrThrArgHisGlyAspThrLeuGluGlyAlaArgGluLeuIleArgVal
ThrIleSerIleLeuAspMETGluThrProLeuLysAlaProGluSerSerLeuGlySer
LeuTyrLeuTyr---ThrTrpArgHisPro---ArgArgGlnArgAlaHis---GlyPro
```

FIG. 5q

```
       5890      5900      5910      5920      5930      5940
         |         |         |         |         |         |
CTACAACGAGCCCTCTTCACGCACTTCAGAGCAGGATGTGGCCACTCAAGAATTGGCCAA

LeuGlnArgAlaLeuPheThrHisPheArgAlaGlyCysGlyHisSerArgIleGlyGln
 TyrAsnGluProSerSerArgThrSerGluGlnAspValAlaThrGlnGluLeuAlaAsn
  ThrThrSerProLeuHisAlaLeuGlnSerArgMETTrpProLeuLysAsnTrpProThr 5950      5960      5970      5980      5990      6000
         |         |         |         |         |         |
CCAAGGGGAAGAAATCCTCTCTCAGCTATACCGACCCCTAGAAACATGCAATAACAAATG

ProArgGlyArgAsnProLeuSerAlaIleProThrProArgAsnMETGln---GlnMET
 GlnGlyGluGluIleLeuSerGlnLeuTyrArgProLeuGluThrCysAsnAsnLysCys
  LysGlyLysLysSerSerLeuSerTyrThrAspPro---LysHisAlaIleThrAsnAla 6010      6020      6030      6040      6050      6060
         |         |         |         |         |         |
CTTTTGTAAGGGGTGCTGCTTCCATTGCCAGCTGTGTTTTTTAAACAAGGGGCTCGGGAT

LeuLeu---GlyValLeuLeuProLeuProAlaValPhePheLysGlnGlyAlaArgAsp
 PheCysLysGlyCysCysPheHisCysGlnLeuCysPheLeuAsnLysGlyLeuGlyIle
  PheValArgGlyAlaAlaSerIleAlaSerCysValPhe---ThrArgGlySerGlyTyr 6070      6080      6090      6100      6110      6120
         |         |         |         |         |         |
ATGTTATGACCGAAAGGGCAGACGAAGAAGGAGTCCGAAGAAAACTAAGGCTCATTCGTC

METLeu---ProLysGlyGlnThrLysLysGluSerGluGluAsn---GlySerPheVal
 CysTyrAspArgLysGlyArgArgArgArgSerProLysLysThrLysAlaHisSerSer
  ValMETThrGluArgAlaAspGluGluGlyValArgArgLysLeuArgLeuIleArgLeu 6130      6140      6150      6160      6170      6180
         |         |         |         |         |         |
TCCTGCATCAGACAAGTGAGTACAATGAGTGGTAAAATTCAGCTGCTTGTTGCCTTTCTG

SerCysIleArgGlnValSerThrMETSerGlyLysIleGlnLeuLeuValAlaPheLeu
 ProAlaSerAspLys---ValGln---ValValLysPheSerCysLeuLeuProPheCys
  LeuHisGlnThrSerGluTyrAsnGluTrp---AsnSerAlaAlaCysCysLeuSerAla 6190      6200      6210      6220      6230      6240
         |         |         |         |         |         |
CTAACTAGTGCTTGCTTAATATATTGCACCAAATATGTGACTGTTTTCTATGGAGTACCC

LeuThrSerAlaCysLeuIleTyrCysThrLysTyrValThrValPheTyrGlyValPro
 ---LeuValLeuAla---TyrIleAlaProAsnMET---LeuPheSerMETGluTyrPro
  Asn---CysLeuLeuAsnIleLeuHisGlnIleCysAspCysPheLeuTrpSerThrArg
```

FIG. 5r

```
       6250      6260      6270      6280      6290      6300
         |         |         |         |         |         |
GTGTGGAAAAATGCATCCATTCCCCTCTTTTGTGCAACTAAAAATAGAGATACTTGGGGA
```

ValTrpLysAsnAlaSerIleProLeuPheCysAlaThrLysAsnArgAspThrTrpGly
CysGlyLysMETHisProPheProSerPheValGlnLeuLysIleGluIleLeuGlyGlu
ValGluLysCysIleHisSerProLeuLeuCysAsn---Lys---ArgTyrLeuGlyAsn

```
       6310      6320      6330      6340      6350      6360
         |         |         |         |         |         |
ACCATACAGTGCTTGCCAGACAATGATGATTATCAAGAGATACCTTTGAATGTAACAGAG
```

ThrIleGlnCysLeuProAspAsnAspAspTyrGlnGluIleProLeuAsnValThrGlu
ProTyrSerAlaCysGlnThrMETMETIleIleLysArgTyrLeu---MET---GlnArg
HisThrValLeuAlaArgGln------LeuSerArgAspThrPheGluCysAsnArgGly

```
       6370      6380      6390      6400      6410      6420
         |         |         |         |         |         |
GCTTTTGACGCATGGGATAATATAGTAACAGAACAAGCAGTAGAAGATGTCTGGAATCTA
```

AlaPheAspAlaTrpAspAsnIleValThrGluGlnAlaValGluAspValTrpAsnLeu
LeuLeuThrHisGlyIleIle------GlnAsnLysGln---LysMETSerGlyIleTyr
Phe---ArgMETGly---TyrSerAsnArgThrSerSerArgArgCysLeuGluSerIle

```
       6430      6440      6450      6460      6470      6480
         |         |         |         |         |         |
TTTGAGACATCAATAAAACCATGTGTCAAATTAACGCCTTTATGTGTAACAATGAACTGT
```

PheGluThrSerIleLysProCysValLysLeuThrProLeuCysValThrMETAsnCys
LeuArgHisGln---AsnHisValSerAsn---ArgLeuTyrVal---Gln---ThrVal
---AspIleAsnLysThrMETCysGlnIleAsnAlaPheMETCysAsnAsnGluLeu---

```
       6490      6500      6510      6520      6530      6540
         |         |         |         |         |         |
AACGCAAGTACAGAGAGCGCAGTTGCAACTACAAGCCCATCTGGACCTGATATGATAAAT
```

AsnAlaSerThrGluSerAlaValAlaThrThrSerProSerGlyProAspMETIleAsn
ThrGlnValGlnArgAlaGlnLeuGlnLeuGlnAlaHisLeuAspLeuIle------MET
ArgLysTyrArgGluArgSerCysAsnTyrLysProIleTrpThr---TyrAspLys---

```
       6550      6560      6570      6580      6590      6600
         |         |         |         |         |         |
GATACTGATCCATGCATACAATTGAACAATTGCTCAGGACTGAGGGAGGAAGACATGGTC
```

AspThrAspProCysIleGlnLeuAsnAsnCysSerGlyLeuArgGluGluAspMETVal
IleLeuIleHisAlaTyrAsn---ThrIleAlaGlnAsp---GlyArgLysThrTrpSer
Tyr---SerMETHisThrIleGluGlnLeuLeuArgThrGluGlyGlyArgHisGlyArg

FIG. 5s

```
               6610      6620      6630      6640      6650      6660
                |         |         |         |         |         |
       GAGTGTCAGTTCAATATGACAGGACTAGAGTTAGATAAGAAAAAACAGTATAGTGAAACC
```

GluCysGlnPheAsnMETThrGlyLeuGluLeuAspLysLysLysGlnTyrSerGluThr
 SerValSerSerIle---GlnAsp---Ser---IleArgLysAsnSerIleValLysPro
 ValSerValGlnTyrAspArgThrArgValArg---GluLysThrVal------AsnLeu

```
               6670      6680      6690      6700      6710      6720
                |         |         |         |         |         |
       TGGTACTCAAAAGATGTGGTTTGTGAATCAGATAACAGCACAGACCGAAAAAGATGTTAC
```

TrpTyrSerLysAspValValCysGluSerAspAsnSerThrAspArgLysArgCysTyr
 GlyThrGlnLysMETTrpPheValAsnGlnIleThrAlaGlnThrGluLysAspValThr
 ValLeuLysArgCysGlyLeu---IleArg---GlnHisArgProLysLysMETLeuHis

```
               6730      6740      6750      6760      6770      6780
                |         |         |         |         |         |
       ATGAACCATTGCAACACATCAGTCATCACAGAGTCATGTGACAAGCACTATTGGGATGCT
```

METAsnHisCysAsnThrSerValIleThrGluSerCysAspLysHisTyrTrpAspAla
 ---ThrIleAlaThrHisGlnSerSerGlnSerHisValThrSerThrIleGlyMETLeu
 GluProLeuGlnHisIleSerHisHisArgValMET---GlnAlaLeuLeuGlyCysTyr

```
               6790      6800      6810      6820      6830      6840
                |         |         |         |         |         |
       ATGAGATTTAGATACTGTGCACCACCGGGTTTTGTCTTGCTAAGGTGCAATGATACCAAT
```

METArgPheArgTyrCysAlaProProGlyPheValLeuLeuArgCysAsnAspThrAsn
 ---AspLeuAspThrValHisHisArgValLeuSerCys---GlyAlaMETIleProIle
 GluIle---IleLeuCysThrThrGlyPheCysLeuAlaLysValGln---TyrGlnLeu

```
               6850      6860      6870      6880      6890      6900
                |         |         |         |         |         |
       TACTCAGGCTTTGAGCCCAATTGCTCTAAAGTAGTAGCTTCTACATGTACAAGAATGATG
```

TyrSerGlyPheGluProAsnCysSerLysValValAlaSerThrCysThrArgMETMET
 ThrGlnAlaLeuSerProIleAlaLeuLys------LeuLeuHisValGlnGlu---Trp
 LeuArgLeu---AlaGlnLeuLeu---SerSerSerPheTyrMETTyrLysAsnAspGly

```
               6910      6920      6930      6940      6950      6960
                |         |         |         |         |         |
       GAAACGCAACCTTCTACTTGGCTTGGCTTTAATGGCACTAGGGCAGAAAATAGAACATAT
```

GluThrGlnProSerThrTrpLeuGlyPheAsnGlyThrArgAlaGluAsnArgThrTyr
 LysArgAsnLeuLeuLeuGlyLeuAlaLeuMETAlaLeuGlyGlnLysIleGluHisIle
 AsnAlaThrPheTyrLeuAlaTrpLeu---TrpHis---GlyArgLys---AsnIleTyr

FIG. 5t

```
              6970       6980      6990       7000       7010       7020
               |          |         |          |          |          |
     ATCTATTGGCATGGTAGGGATAACAGAACTATTATCAGCTTAAACAAATATTATAATCTC

IleTyrTrpHisGlyArgAspAsnArgThrIleIleSerLeuAsnLysTyrTyrAsnLeu
     SerIleGlyMETValGlyIleThrGluLeuLeuSerAla---ThrAsnIleIleIleSer
     LeuLeuAlaTrp---Gly---GlnAsnTyrTyrGlnLeuLysGlnIleLeu---SerHis 7030       7040      7050       7060       7070       7080
               |          |         |          |          |          |
     ACCATACTTTGTAGGAGACCAGAAAATAAAACAGTTGTACCAATAACACTCATGTCAGGC

ThrIleLeuCysArgArgProGluAsnLysThrValValProIleThrLeuMETSerGly
     ProTyrPheValGlyAspGlnLysIleLysGlnLeuTyrGln---HisSerCysGlnAla
     HisThrLeu---GluThrArgLys---AsnSerCysThrAsnAsnThrHisValArgPro 7090       7100      7110       7120       7130       7140
               |          |         |          |          |          |
     CGCAGATTTCACTCCCAGAAGATCATCAATAAAAAACCCAGGCAAGCATGGTGCCGGTTC

ArgArgPheHisSerGlnLysIleIleAsnLysLysProArgGlnAlaTrpCysArgPhe
     AlaAspPheThrProArgArgSerSerIleLysAsnProGlyLysHisGlyAlaGlySer
     GlnIleSerLeuProGluAspHisGln---LysThrGlnAlaSerMETValProValGln 7150       7160      7170       7180       7190       7200
               |          |         |          |.         |          |
     AAAGGCGAGTGGAGGGAAGCCATGCAGGAGGTGAAACAAACCCTTGTAAAACATCCCAGG

LysGlyGluTrpArgGluAlaMETGlnGluValLysGlnThrLeuValLysHisProArg
     LysAlaSerGlyGlyLysProCysArgArg---AsnLysProLeu---AsnIleProGly
     ArgArgValGluGlySerHisAlaGlyGlyGluThrAsnProCysLysThrSerGlnVal 7210       7220      7230       7240       7250       7260
               |          |         |          |          |          |
     TATAAAGGAACCAATGACACAAATAAAATTAACTTTACAGCACCAGAAAAAGACTCAGAC

TyrLysGlyThrAsnAspThrAsnLysIleAsnPheThrAlaProGluLysAspSerAsp
     IleLysGluProMETThrGlnIleLysLeuThrLeuGlnHisGlnLysLysThrGlnThr
     ---ArgAsnGln---HisLys---Asn---LeuTyrSerThrArgLysArgLeuArgPro 7270       7280      7290       7300       7310       7320
               |          |         |          |          |          |
     CCAGAAGTAGCATATATGTGGACTAACTGCAGAGGAGAATTCCTCTATTGCAACATGACT

ProGluValAlaTyrMETTrpThrAsnCysArgGlyGluPheLeuTyrCysAsnMETThr
     GlnLys---HisIleCysGlyLeuThrAlaGluGluAsnSerSerIleAlaThr---Leu
     ArgSerSerIleTyrValAsp---LeuGlnArgArgIleProLeuLeuGlnHisAspLeu
```

FIG. 5u

```
            7330       7340       7350       7360       7370       7380
              |          |          |          |          |          |
    TGGTTCCTTAATTGGGTAGAAAACAAGACGGGTCAACAGCATAACTATGTGCCGTGCCAT
```

TrpPheLeuAsnTrpValGluAsnLysThrGlyGlnGlnHisAsnTyrValProCysHis
 GlySerLeuIleGly---LysThrArgArgValAsnSerIleThrMETCysArgAlaIle
  ValPro---LeuGlyArgLysGlnAspGlySerThrAla---LeuCysAlaValProTyr

```
            7390       7400       7410       7420       7430       7440
              |          |          |          |          |          |
    ATAGAGCAAATAATTAATACCTGGCATAAGGTAGGGAAAAATGTATATTTGCCTCCTAGG
```

IleGluGlnIleIleAsnThrTrpHisLysValGlyLysAsnValTyrLeuProProArg
 ---SerLys---LeuIleProGlyIleArg---GlyLysMETTyrIleCysLeuLeuGly
  ArgAlaAsnAsn---TyrLeuAla---GlyArgGluLysCysIlePheAlaSer---Gly

```
            7450       7460       7470       7480       7490       7500
              |          |          |          |          |          |
    GAAGGAGAGTTGTCCTGCGAATCAACAGTGACCAGTATCATTGCTAACATTGATGTTGAT
```

GluGlyGluLeuSerCysGluSerThrValThrSerIleIleAlaAsnIleAspValAsp
 LysGluSerCysProAlaAsnGlnGln---ProValSerLeuLeuThrLeuMETLeuMET
  ArgArgValValLeuArgIleAsnSerAspGlnTyrHisCys---His---Cys---Trp

```
            7510       7520       7530       7540       7550       7560
              |          |          |          |          |          |
    GGAGATAACCGGACAAATATTACCTTTAGTGCAGAGGTGGCAGAACTATACCGATTGGAA
```

GlyAspAsnArgThrAsnIleThrPheSerAlaGluValAlaGluLeuTyrArgLeuGlu
 GluIleThrGlyGlnIleLeuProLeuValGlnArgTrpGlnAsnTyrThrAspTrpAsn
  Arg---ProAspLysTyrTyrLeu---CysArgGlyGlyArgThrIleProIleGlyIle

```
            7570       7580       7590       7600       7610       7620
              |          |          |          |          |          |
    TTGGGGGATTATAAATTAGTAGAAGTAACACCAATTGGCTTCGCCCCTACAGCAGAAAAA
```

LeuGlyAspTyrLysLeuValGluValThrProIleGlyPheAlaProThrAlaGluLys
 TrpGlyIleIleAsn------Lys---HisGlnLeuAlaSerProLeuGlnGlnLysLys
  GlyGlyLeu---IleSerArgSerAsnThrAsnTrpLeuArgProTyrSerArgLysLys

```
            7630       7640       7650       7660       7670       7680
              |          |          |          |          |          |
    AGATACTCCTCTGCTCCAGGGAGACATAAGAGAGGTGTGCTTGTGCTAGGGTTCCTAGGT
```

ArgTyrSerSerAlaProGlyArgHisLysArgGlyValLeuValLeuGlyPheLeuGly
 AspThrProLeuLeuGlnGlyAspIleArgGluValCysLeuCys---GlySer---Val
  IleLeuLeuCysSerArgGluThr---GluArgCysAlaCysAlaArgValProArgPhe

FIG. 5v

```
         7690      7700      7710      7720      7730      7740
          |         |         |         |         |         |
TTTCTCACGACAGCAGGTGCTGCAATGGGGGCGGCGTCTCTGACGCTGTCGGCTCAGTCT
```

PheLeuThrThrAlaGlyAlaAlaMETGlyAlaAlaSerLeuThrLeuSerAlaGlnSer
PheSerArgGlnGlnValLeuGlnTrpGlyArgArgLeu---ArgCysArgLeuSerLeu
SerHisAspSerArgCysCysAsnGlyGlyGlyValSerAspAlaValGlySerValSer

```
         7750      7760      7770      7780      7790      7800
          |         |         |         |         |         |
CGGACTTTATTCCGTGGGATAGTGCAGCAACAGCAACAGCTGTTGGACGTGGTCAAGAGA
```

ArgThrLeuPheArgGlyIleValGlnGlnGlnGlnGlnLeuLeuAspValValLysArg
GlyLeuTyrSerValGly---CysSerAsnSerAsnSerCysTrpThrTrpSerArgAsp
AspPheIleProTrpAspSerAlaAlaThrAlaThrAlaValGlyArgGlyGlnGluThr

```
         7810      7820      7830      7840      7850      7860
          |         |         |         |         |         |
CAACAAGAAATGTTGCGACTGACCGTCTGGGGAACTAAAAACCTCCAGGCAAGAGTCACT
```

GlnGlnGluMETLeuArgLeuThrValTrpGlyThrLysAsnLeuGlnAlaArgValThr
AsnLysLysCysCysAsp---ProSerGlyGluLeuLysThrSerArgGlnGluSerLeu
ThrArgAsnValAlaThrAspArgLeuGlyAsn---LysProProGlyLysSerHisCys

```
         7870      7880      7890      7900      7910      7920
          |         |         |         |         |         |
GCTATTGAGAAGTACCTAGCAGACCAGGCGCGACTAAATTCATGGGGATGTGCGTTTAGA
```

AlaIleGluLysTyrLeuAlaAspGlnAlaArgLeuAsnSerTrpGlyCysAlaPheArg
LeuLeuArgSerThr---GlnThrArgArgAsp---IleHisGlyAspValArgLeuAsp
Tyr---GluValProSerArgProGlyAlaThrLysPheMETGlyMETCysVal---Thr

```
         7930      7940      7950      7960      7970      7980
          |         |         |         |         |         |
CAAGTCTGCCACACTACTGTACCATGGGTAAATGACACCTTAACACCTGAGTGGAACAAC
```

GlnValCysHisThrThrValProTrpValAsnAspThrLeuThrProGluTrpAsnAsn
LysSerAlaThrLeuLeuTyrHisGly---METThrPro---HisLeuSerGlyThrThr
SerLeuProHisTyrCysThrMETGlyLys---HisLeuAsnThr---ValGluGlnHis

```
         7990      8000      8010      8020      8030      8040
          |         |         |         |         |         |
ATGACATGGCAAGAATGGGAACACAAAATCCGCTTCCTAGAGGCAAATATCAGTGAGAGT
```

METThrTrpGlnGluTrpGluHisLysIleArgPheLeuGluAlaAsnIleSerGluSer
---HisGlyLysAsnGlyAsnThrLysSerAlaSer---ArgGlnIleSerValArgVal
AspMETAlaArgMETGlyThrGlnAsnProLeuProArgGlyLysTyrGln---GluPhe

```
         8050      8060      8070      8080      8090      8100
          |         |         |         |         |         |
TTAGAACAGGCACAAATCCAGCAAGAAAAGAATATGTATGAGCTGCAAAAGCTAAATAGC
```

LeuGluGlnAlaGlnIleGlnGlnGluLysAsnMETTyrGluLeuGlnLysLeuAsnSer
---AsnArgHisLysSerSerLysLysArgIleCysMETSerCysLysSer---IleAla
ArgThrGlyThrAsnProAlaArgLysGluTyrVal---AlaAlaLysAlaLys---Leu

FIG. 5w

```
        8110      8120      8130      8140      8150      8160
         |         |         |         |         |         |
TGGGATGTTTTTGGCAATTGGTTTGACTTAACCTCCTGGATCAAGTATATTCAATATGGA

TrpAspValPheGlyAsnTrpPheAspLeuThrSerTrpIleLysTyrIleGlnTyrGly
 GlyMETPheLeuAlaIleGlyLeuThr---ProProGlySerSerIlePheAsnMETGlu
  GlyCysPheTrpGlnLeuVal---LeuAsnLeuLeuAspGlnValTyrSerIleTrpSer 8170      8180      8190      8200      8210      8220
         |         |         |         |         |         |
GTCATGATAGTAGTAGGAATAGTAGCTCTCAGAATAGTAATATATGTAGTACAAATGCTA

ValMETIleValValGlyIleValAlaLeuArgIleValIleTyrValValGlnMETLeu
 Ser------------Glu------LeuSerGlu------TyrMET---TyrLysCys---
  HisAspSerSerArgAsnSerSerSerGlnAsnSerAsnIleCysSerThrAsnAlaLys 8230      8240      8250      8260      8270      8280
         |         |         |         |         |         |
AGTAGACTTAGAAAAGGCTATAGGCCTGTTTCTCTTCCCCCCGGTTATATTCAACAGATC

SerArgLeuArgLysGlyTyrArgProValSerLeuProProGlyTyrIleGlnGlnIle
 ValAspLeuGluLysAlaIleGlyLeuPheLeuPheProProValIlePheAsnArgSer
  ---Thr---LysArgLeu---AlaCysPheSerSerProArgLeuTyrSerThrAspPro 8290      8300      8310      8320      8330      8340
         |         |         |         |         |         |
CATATCCACAAGGACTGGGAACAGCCAGACAGAGAAGAAACAGAAGAAGACGTTGGGAAC

HisIleHisLysAspTrpGluGlnProAspArgGluGluThrGluGluAspValGlyAsn
 IleSerThrArgThrGlyAsnSerGlnThrGluLysLysGlnLysLysThrLeuGlyThr
  TyrProGlnGlyLeuGlyThrAlaArgGlnArgArgAsnArgArgArgTrpGluArg 8350      8360      8370      8380      8390      8400
         |         |         |         |         |         |
ACGTTGGAAGCAGATCCTGGCCTTGGCCGATAGAATATATACATTTCCTGATCCGCCTG spValGlySerArgSerTrpProTrpProIleGluTyrIleHisPheLeuIleArgLeu
 ThrLeuGluAlaAspProGlyLeuGlyArg---AsnIleTyrIleSer---SerAlaCys
  ArgTrpLysGlnIleLeuAlaLeuAlaAspArgIleTyrThrPheProAspProProAla 8410      8420      8430      8440      8450      8460
         |         |         |         |         |         |
TGATCCGCCCTCTTGACCAGACTATACAACAGCTGCAGGGACTTACTATCCAGACTCTAC euIleArgLeuLeuThrArgLeuTyrAsnSerCysArgAspLeuLeuSerArgLeuTyr
 ---SerAlaSer---ProAspTyrThrThrAlaAlaGlyThrTyrTyrProAspSerThr
  AspProProLeuAspGlnThrIleGlnGlnLeuGlnGlyLeuThrIleGlnThrLeuPro
```

FIG. 5x

```
        8470      8480      8490      8500      8510      8520
         |         |         |         |         |         |
       GATCCTCCAACCACTCAGAGACTGGCTGAGACTCAAGGCAGCCTACCTGCAGTATGGG uIleLeuGlnProLeuArgAspTrpLeuArgLeuLysAlaAlaTyrLeuGlnTyrGly
   --SerSerAsnHisSerGluThrGly---AspSerArgGlnProThrCysSerMETGly
   AspProProThrThrGlnArgLeuAlaGluThrGlnGlySerLeuProAlaValTrpVal 8530      8540      8550      8560      8570      8580
         |         |         |         |         |         |
       CGAGTGGATCCAAGAAGCGTTCCAGGCCCTCGCGAGGGTTACAAGAGAGACTCTTACG sGluTrpIleGlnGluAlaPheGlnAlaLeuAlaArgValThrArgGluThrLeuThr
   laSerGlySerLysLysArgSerArgProSerArgGlyLeuGlnGluArgLeuLeuArg
   ArgValAspProArgSerValProGlyProArgGluGlyTyrLysArgAspSerTyrGlu 8590      8600      8610      8620      8630      8640
         |         |         |         |         |         |
       CGCGGGGAGGAGCTTGTGGGGGGCTCTGGGACGAATCGGAAGGGGGATACTCGCAGTT rAlaGlyArgSerLeuTrpGlyAlaLeuGlyArgIleGlyArgGlyIleLeuAlaVal
   laArgGlyGlyAlaCysGlyGlyLeuTrpAspGluSerGluGlyGlyTyrSerGlnPhe
   ArgGlyGluGluLeuValGlyGlySerGlyThrAsnArgLysGlyAspThrArgSerSer 8650      8660      8670      8680      8690      8700
         |         |         |         |         |         |
       CCACGAAGGATCAGGCAGGGAGCAGAAATTGCCCTCCTGTGAGGGACAGAGATATCAGCA

ProArgArgIleArgGlnGlyAlaGluIleAlaLeuLeu---GlyThrGluIleSerAla
   HisGluGlySerGlyArgGluGlnLysLeuProSerCysGluGlyGlnArgTyrGlnGln
   ThrLysAspGlnAlaGlySerArgAsnCysProProValArgAspArgAspIleSerLys 8710      8720      8730      8740      8750      8760
         |         |         |         |         |         |
       AGGAGACTTTATGAATACCCCATGGAGAACCCCAGCAACAGAAAAGGAAAAAGAATCGTA

ArgArgLeuTyrGluTyrProMETGluAsnProSerAsnArgLysGlyLysArgIleVal
   GlyAspPheMETAsnThrProTrpArgThrProAlaThrGluLysGluLysGluSerTyr
   GluThrLeu---IleProHisGlyGluProGlnGlnGlnLysArgLysLysAsnArgThr 8770      8780      8790      8800      8810      8820
         |         |         |         |         |         |
       CAGGCAACAAAATATGGATGATGTAGATTCAGATGATGATGACCTAGTAGGGGTCTCTGA

GlnAlaThrLysTyrGly---CysArgPheArg---------ProSerArgGlyLeu---
   ArgGlnGlnAsnMETAspAspValAspSerAspAspAspAspLeuValGlyValSerAsp
   GlyAsnLysIleTrpMETMET---IleGlnMETMETMETThr------GlySerLeuThr 8830      8840      8850      8860      8870      8880
         |         |         |         |         |         |
       CACATCAAGAGTACCATTGAGAGCAATGACATATAGAATGGCAGTAGACATGTCAGATTT

HisIleLysSerThrIleGluSerAsnAspIle---AsnGlySerArgHisValArgPhe
   ThrSerArgValProLeuArgAlaMETThrTyrArgMETAlaValAspMETSerAspLeu
   HisGlnGluTyrHis---GluGln---HisIleGluTrpGln---ThrCysGlnIle---
```

FIG. 5y

```
        8890      8900      8910      8920      8930      8940
         |         |         |         |         |         |
    AATAAAAGATAAGGGGGGACTGGAAGGGATGTATTACAGTGAGAGAAGACATAGAATCCT

AsnLysArg---GlyGlyThrGlyArgAspValLeuGln---GluLysThr----AsnPro
    IleLysAspLysGlyGlyLeuGluGlyMETTyrTyrSerGluArgArgHisArgIleLeu
    ---LysIleArgGlyAspTrpLysGlyCysIleThrValArgGluAspIleGluSer---

8950      8960      8970      8980      8990      9000
         |         |         |         |         |         |
    AGACATATACTTAGAAAAGGAAGAAGGGATAATTCCAGATTGGCAGAACTATACTCATGG

ArgHisIleLeuArgLysGlyArgArgAspAsnSerArgLeuAlaGluLeuTyrSerTrp
    AspIleTyrLeuGluLysGluGluGlyIleIleProAspTrpGlnAsnTyrThrHisGly
    ThrTyrThr---LysArgLysLysGly---PheGlnIleGlyArgThrIleLeuMETGly 9010      9020      9030      9040      9050      9060
         |         |         |         |         |         |
    GCTAGGAGTAAGGTACCCAATGTTCTTTGGGTGGCTATGGAAGCTAGTACCAGTAACTGT

AlaArgSerLysValProAsnValLeuTrpValAlaMETGluAlaSerThrSerAsnCys
    LeuGlyValArgTyrProMETPhePheGlyTrpLeuTrpLysLeuValProValThrVal
    ---Glu---GlyThrGlnCysSerLeuGlyGlyTyrGlySer---TyrGln---LeuSer 9070      9080      9090      9100      9110      9120
         |         |         |         |         |         |
    CCCACAAGAAGGGGAGGACACTGAGACTCTCTGCTTAATGCACTCAGCACAAGTAAGCAG

ProThrArgArgGlyGlyHis---AspSerLeuLeuAsnAlaLeuSerThrSerLysGln
    ProGlnGluGlyGluAspThrGluThrLeuCysLeuMETHisSerAlaGlnValSerArg
    HisLysLysGlyArgThrLeuArgLeuSerAla---CysThrGlnHisLys---AlaAsp 9130      9140      9150      9160      9170      9180
         |         |         |         |         |         |
    ATTTGATGACCCGCATGGGGAGACACTAGTCTGGAAGTTTGACCCCATGCTGGCTCATGA

Ile------ProAlaTrpGlyAspThrSerLeuGluVal---ProHisAlaGlySer---
    PheAspAspProHisGlyGluThrLeuValTrpLysPheAspProMETLeuAlaHisGlu
    LeuMETThrArgMETGlyArgHis---SerGlySerLeuThrProCysTrpLeuMETSer 9190      9200      9210      9220      9230      9240
         |         |         |         |         |         |
    GTACACGACCTTTATTCTATACCCAGAGGAATTTGGGCACAAGTCAGGAATGGAAGAAGA

ValHisAspLeuTyrSerIleProArgGlyIleTrpAlaGlnValArgAsnGlyArgArg
    TyrThrThrPheIleLeuTyrProGluGluPheGlyHisLysSerGlyMETGluGluAsp
    ThrArgProLeuPheTyrThrGlnArgAsnLeuGlyThrSerGlnGluTrpLysLysMET
```

FIG. 5z

```
            9250      9260      9270      9280      9290      9300
             |         |         |         |         |         |
        TGACTGGAAGGCAAAACTGAAAGCAAGAGGGATACCATTTAGTTAAAAACAGGAACAACC

---LeuGluGlyLysThrGluSerLysArgAspThrIle---LeuLysThrGlyThrThr
        AspTrpLysAlaLysLeuLysAlaArgGlyIleProPheSer---LysGlnGluGlnPro
        ThrGlyArgGlnAsn---LysGlnGluGlyTyrHisLeuValLysAsnArgAsnAsnHis 9310      9320      9330      9340      9350      9360
             |         |         |         |         |         |
        ATACTTGGTCAGGACAGGAAGTAGCTACTGAAAACAGCTGAGACTGCAGGGACTTTCCAG

IleLeuGlyGlnAspArgLys---LeuLeuLysThrAlaGluThrAlaGlyThrPheGln
        TyrLeuValArgThrGlySerSerTyr---LysGlnLeuArgLeuGlnGlyLeuSerArg
        ThrTrpSerGlyGlnGluValAlaThrGluAsnSer---AspCysArgAspPheProGlu 9370      9380      9390      9400      9410      9420
             |         |         |         |         |         |
        AAGGGGCTGTAACCAGGGGAGGGACATGGGAGGAGCTGGTGGGGAACGCCCTCATACTTT

LysGlyLeu---ProGlyGluGlyHisGlyArgSerTrpTrpGlyThrProSerTyrPhe
        ArgGlyCysAsnGlnGlyArgAspMETGlyGlyAlaGlyGlyGluArgProHisThrPhe
        GlyAlaValThrArgGlyGlyThrTrpGluGluLeuValGlyAsnAlaLeuIleLeuSer 9430      9440      9450      9460      9470      9480
             |         |         |         |         |         |
        CTGTATAAATGTACCCGCTGCTCGCATTGTATTCAGTCGCTCTGCGGAGAGGCTGGCAGA

LeuTyrLysCysThrArgCysSerHisCysIleGlnSerLeuCysGlyGluAlaGlyArg
        CysIleAsnValProAlaAlaArgIleValPheSerArgSerAlaGluArgLeuAlaAsp
        Val---METTyrProLeuLeuAlaLeuTyrSerValAlaLeuArgArgGlyTrpGlnIle 9490      9500      9510      9520      9530      9540
             |         |         |         |         |         |
        TTGAGCCCTGGGAGGTTCTCTCCAGCACTAGCAGGTAGAGCCTGGGTGTTCCCTGCTGGA

LeuSerProGlyArgPheSerProAlaLeuAlaGlyArgAlaTrpValPheProAlaGly
        ---AlaLeuGlyGlySerLeuGlnHis---GlnValGluProGlyCysSerLeuLeuAsp
        GluProTrpGluValLeuSerSerThrSerArg---SerLeuGlyValProCysTrpThr
```

FIG. 5z cont'd

```
          9550      9560      9570      9580      9590      9600
           |         |         |         |         |         |
       CTCTCACCAGTGCTTGGCCGGCGCTGGGCAGACGGCTCCACGCTTGCTTGCTTAAAAGAC

LeuSerProValLeuGlyArgArgTrpAlaAspGlySerThrLeuAlaCysLeuLysAsp
        SerHisGlnCysLeuAlaGlyAlaGlyGlnThrAlaProArgLeuLeuAla---LysThr
         LeuThrSerAlaTrpProAlaLeuGlyArgArgLeuHisAlaCysLeuLeuLysArgPro

9610     .9620      9630
           |         |         |
       CTCTTAATAAAGCTGCCAGTTAGAAGCAAGTTA

LeuLeuIleLysLeuProValArgSerLysLeu
        Ser------SerCysGlnLeuGluAlaSer
         LeuAsnLysAlaAlaSer---LysGlnVal
```

CHARACTERIZATION OF REPLICATION COMPETENT HUMAN IMMUNODEFICIENCY TYPE 2 PROVIRAL CLONE HIV-2$_{SBL/ISY}$

FIELD OF INVENTION

The present invention relates to the human immunodeficiency virus type 2 (HIV-2) which is associated with the acquired immunodeficiency syndrome (AIDS) in man. The present invention further relates to recombinant DNA technology and its use in the cloning and characterization of a proviral HIV-2 sequence.

BACKGROUND OF INVENTION

Human immunodeficiency viruses type 1 and 2 (HIV-1 and HIV-2) are related retroviruses associated with the acquired immunodeficiency syndrome (AIDS) in man. A virus closely related to HIV-2, SIV$_{mac}$, has been isolated from captive Macaques with AIDS. Other viruses of the same general family have been isolated from both captive and wild Old World monkeys.

The genetic structures of HIV-1 and HIV-2 are more complex than the structures of other animal retroviruses; in addition to the structural genes coding for the core and the envelope proteins, there is a tat gene, a 14Kd protein which acts in trans to increase the expression of viral genes from the viral LTR; a rev gene (19Kd) which differentially regulates the expression of virion protein; a nef gene (27Kd) which reduces viral expression; a vif gene which is essential for the infectivity of cell-free virus; and a vpr gene, the function of which is unknown. One additional gene, vpx, is present in HIV-2 and the related simian virus SIV$_{mac}$, but is not present in HIV-1. The vpx protein (p16 for HIV-2 and p14 for SIV) is associated with mature virions, but its function is as yet unknown.

Most of the gene products that regulate viral expression and replication of HIV-1 are also present in HIV-2. In fact, the putative functional domains of the regulatory proteins are evolutionarily conserved. However, differences in the overall structure of the HIV-2 LTRs, which are larger than the HIV-1 LTRs, account for a variation in the responsive region to the viral transactivator gene (tat). The major structural differences between HIV-1 and HIV-2 appear to be the presence of a gene designated vpu in type 1 viruses, while a second gene designated vpx appears only in type 2 viruses. The amino acid sequences of these genes are not homologous, and their functional equivalence is not yet known.

The functions of the HIV-1/HIV-2 accessory genes have been studied by infection of T-cells in vitro, and it appears that a number of these genes are dispensable in virus replication.

As an object of the present invention, a biologically active HIV-2 clone was sought. The availability of such a replication competent HIV-2 proviral clone would permit the further study of HIV and HIV infection in man, including study of the vpx gene, the role of the "non-essential" HIV-accessory genes in viral replication, and the relevance of the structural differences between HIV-1 and HIV-2 in vivo. Additionally, the regulatory elements of the viral LTRs and their interaction with regulatory proteins in the context of a complete infectious genome could be evaluated.

The value of an infectious HIV-2 clone in developing an animal model for HIV vaccine and therapy studies should also be emphasized. Rapid progress in the development of a protective vaccine against HIV has been impaired by the lack of a suitable and cost effective animal model. Successful infection of non-human primates has been achieved only in chimpanzees and gibbons, which are scarce and therefore costly, and although infection is achieved, no pathogenicity has been observed. Thus, the development of an animal model using a human virus closely related to native HIV would be very valuable.

Finally, in view of the fact that individual isolates of HIV-1 are composed of microvariants with distinct biological properties and susceptibility to given neutralizing sera, and further because the composition of this population presumably drifts due to mutations and selection pressures which arise in response to changes in available target cells and host immunity, the availability of an infectious molecular clone would enable one to measure the genetic evolution of the HIV genome and immunological consequences of this evolution in the infected host.

SUMMARY OF INVENTION

A complete genomic clone of HIV-2 has been constructed using DNA from the neoplastic human cell line HUT78 freshly infected with the HIV-2$_{SBL6669}$ viral isolate. This recombinant phage DNA clone was transfected into the lymphocytes of a CD4 positive HUT78 cell line to test the replication competence of the proviral DNA. The genomic clone, designated HIV-2$_{SBL/ISY}$, yielded retroviral particles after a few weeks of culture.

HIV-2$_{SBL/ISY}$ contains a complete provirus including the cellular flanking sequences. This proviral DNA sequence was determined and compared with the published sequence of two other HIV-2 isolates, namely, HIV-2$_{NIH-Z}$ (Zagury et al., Proc. Natl. Acad. Sci. USA 85:5941–5945 (1988)) and HIV-Z$_{ROD}$ (Guyader et al., Nature 326:662–669 (1987)), as well as SIV$_{MAC}$ (Franchini et al., Nature 328:539–543 (1987)). The degree of variability among these HIV-2 isolates was comparable to that generally observed among the HIV-1 isolates sequenced to date.

Immunologically, the HIV-2$_{SBL/ISY}$ clone is similar to the parental virus HIV-2$_{SBL6669}$ (Albert et al. AIDS Res. Hum. Retroviruses 3:1–10 (1987)), but HIV-2$_{SBL/ISY}$ differs in the envelope-transmembrane protein which is truncated (gp32-34) in the parental virus but not in the proviral clone (gp41). Both the parental and cloned viruses are infectious and cytopathic for some human T-cell lines, induce syncytia and infect the human macrophage cell line U937 in vitro. Infectivity is not restricted to human cells, however. Both HIV-2$_{SBL6669}$ and HIV-2$_{SBL/ISY}$ can also infect and kill fresh peripheral blood T-cells from rhesus macaques in vitro. They also have the apparent ability to productively infect the rhesus macaque in vivo as well.

The studies presented herein suggest that the biologically active clone HIV-2$_{SBL/ISY}$ can be used to generate an animal model for functional studies of HIV genes in vivo, as well as for developing experimental approaches to prevent retroviral infection in man.

BRIEF DESCRIPTION OF THE DRAWINGS

FIGS. 1 a–d. Restriction enzyme analysis of the genomic DNA of the transfected cell line HUT78. The upper portion of the figure represents the endonuclease restriction maps of the proviral HIV-2 clones obtained from the viral isolates and HIV-2$_{SBL6669}$ and HIV-2$_{NIHZ}$. The lower portion of FIG. 1 represents the results of BamHI, XbaI and EcoRI cleavage of the genomic DNAs of the HIV-$2_{SBL6669}$, HIV-$2_{NIHZ}$ and SIV$_{K6W}$ infected cell lines. The second lane of each panel represents the analysis of DNA from the HUT78 cell line tranfected with the proviral clone HIV-$2_{SBL/ISY}$.

FIGS. 3a–b. Analyses of viral proteins. The left and central panels provide a Western blot of total viral proteins obtained from disrupted HIV-$2_{SBL/ISY}$ and SIV virions, respectively. The right panel provides the results of an immunoprecipitation of metabolically labelled HIV-$2_{SBL/ISY}$ virions The molecular weight of the proteins was calculated with respect to the relative migration of the protein marker (Rainbow, BRL, Bethesda, Md.).

FIGS. 5a–z. Proviral DNA sequence of HIV-$2_{SBL/ISY}$. This figure shows the translation of the DNA sequence of HIV-$2_{SBL/ISY}$ by nucleotide and amino acid.

DETAILED DESCRIPTION OF THE INVENTION

Figure 2:
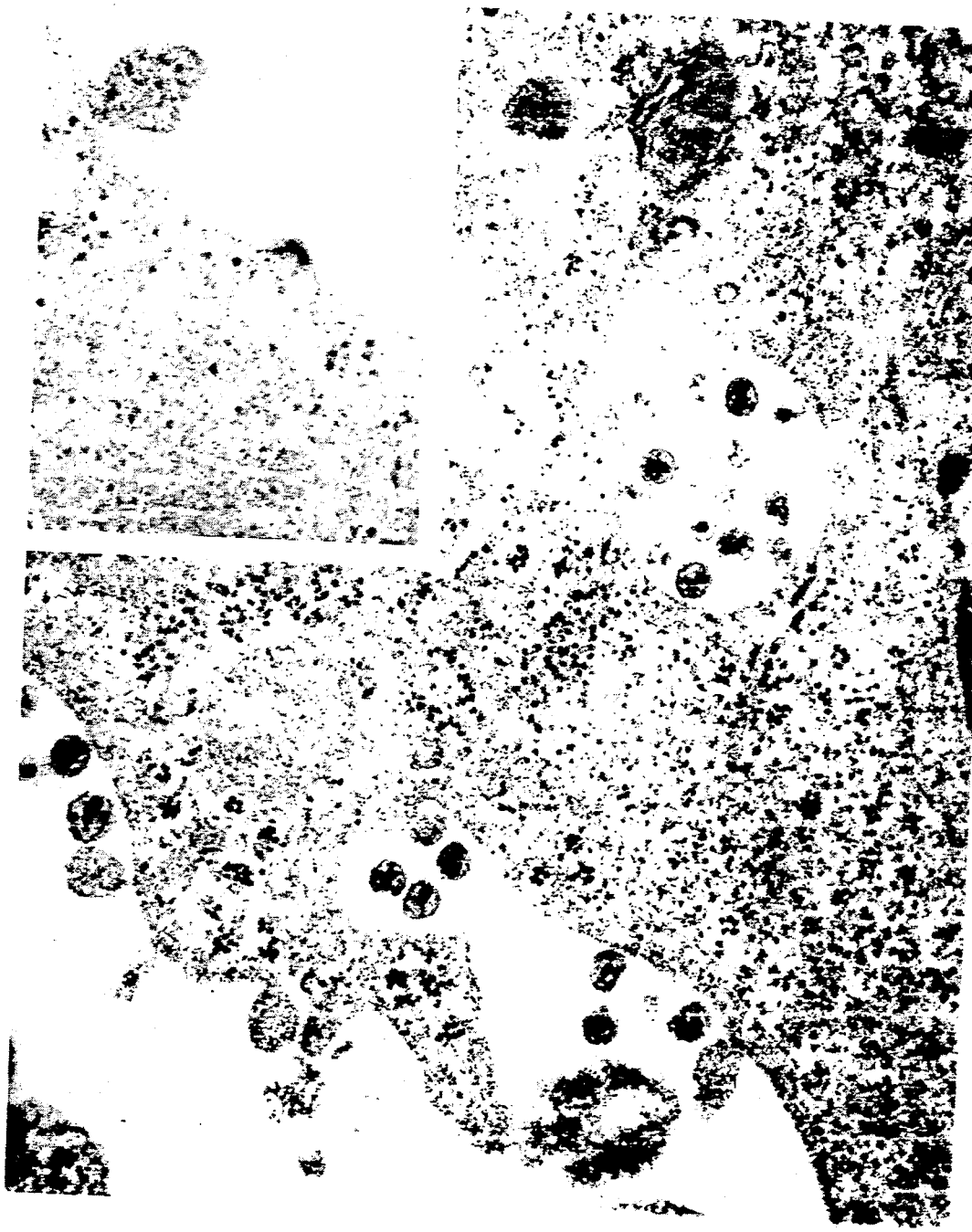
FIG. 2 Electron micrograph of the HIV-2SBL/ISY. Several mature virions with dense cylindrical or round core (depending on the plane of the section) are shown in this figure. Additionally, the inset provides a view in which a budding viral particle from a HUT78 cell can be seen.

All references disclosed below are to be specifically incorporated into the specification by reference.

A. Isolation of Proviral HIV-2 DNA

A phage library was constructed from genomic DNA of the human T-cell line HUT78 (AIDS Research and Reference Reagents Program ("ARRRP"), ERCI Facilities Service Corp., Rockville, Md. - catalogue #89) infected with HIV-$2_{SBL6669}$ (Sarngadharan et al., Science 224:506–508 (1984)). The DNA was partially digested with Sau3A then fractionated on a linear 10–40% sucrose gradient and the 20Kb fraction ligated to EMBL-3 arms (Maniatis et al., *Molecular Cloning: A Laboratory Manual.* New York, Cold Spring Harbor Press, pp. 282–285 (1982)). The ligated DNA was packaged in vitro using the Stratagene gigapack (Stratagene, La Jolla, Calif.) according to the manufacturer's instructions. Recombinant lambda phage clones were obtained from the resulting library using the SIV gag (B16) and envelope (SS35) probes described by Franchini et al. in AIDS Res. Hum. Retroviruses 3:11-17 (1987). A positive clone was isolated which contains a complete provirus, this clone was designated HIV-$2_{SBL/ISY}$. The HIV-$2_{SBL/ISY}$ clone has been deposited at the ATCC (Rockville, Md.) under Accession No. 40505.

The restriction enzyme map of the HIV-$2_{SBL/ISY}$ and HIV-$2_{NIH-Z}$ clones are presented in the upper portion of FIG. 1. As clearly shown, the restriction pattern of HIV-$2_{SBL/ISY}$ differs considerably from that of HIV-$2_{NIH-Z}$, a HIV-2 proviral clone obtained from the viral isolate HIV-$2_{NIHZ}$. Additionally, the restriction pattern of HIV-$2_{SBL/ISY}$ also differs considerably from that of HIV-$2_{ROD}$ and SIV$_{mac}$, data not shown.

The HIV-$2_{SBL/ISY}$ clone was purified and the insert DNA used to generate subclones in the Bluescript vector (Strategene) according to the method of Maniatis et al., supra. These subclones were then employed in dideoxy chain termination sequencing using Sequenase (US Biochemical Corp., Cleveland, Ohio) according to the method of Tabor & Richardson, Proc. Natl. Acad. Sci. USA 84:4767–4771 (1987), and Sanger et al., Proc. Natl. Acad. Sci. USA 74:5463–5467 (1977). Maxam and Gilbert sequencing of the proviral sequence was also performed as described in Proc. Natl. Acad. Sci. USA 74:560–563 (1977).

The HIV-$2_{SBL/ISY}$ proviral sequence has been deposited in the EMBL/GEN Bank under Accession No. J04458. The sequence (nucleotide and amino acid) is depicted in FIG. 5.

The complete DNA sequence of HIV-$2_{SBL/ISY}$ was compared with that of HIV-$2_{NIH-Z}$ and HIV-$2_{ROD}$. The HIV-2 sequences displayed a considerable degree of variation; a result also found among HIV-I sequences.

B. Southern Blot Analysis of HIV-2 Infected Cells

Total cellular DNA from cell lines infected with HIV-$2_{SBL6669}$, HIV-$2_{NIHZ}$ and HIV-$2_{SBL/ISY}$ was digested with BamHI, XbaI, and EcoRI and electrophoresed on 0.8% agarose gel. As a control, the DNA of SIV$_{mac}$ infected cells was also cleaved with these same enzymes and electrophoresed.

Following electrophoresis, the gel was denatured, neutralized, blotted onto nitrocellulose filters as described by Southern (J. Mol. Biol. 98:503–517 (1975)), and hybridized to the labelled probes B16 or SS35 as described by Maniatis et al., supra.

Analysis of the Southern blots indicated the presence of viral sequences as shown in the lower portion of FIG. 1. Hybridization of XbaI and EcoRI cleaved DNAs to the B16 probe, a probe derived from the SIV qaq gene, revealed the same internal bands for the uncloned parental HIV-$2_{SBL6669}$ and the HIV-$2_{SBL/ISY}$ proviral DNA, indicating that HIV-$2_{SBL/ISY}$ is representative of the majority of genotypes present in a cell line infected with the parental virus.

Different restriction patterns were observed with the genomic DNA from the SIV and the HIV-$2_{NIH-Z}$ infected cell lines. DNA samples cleaved with BamHI and hybridized with SS35, a SIV envelope probe, yielded the same internal 5Kd band in both HIV-2 clones, as well as the expected 8.5 Kd band in SIV.

C. DNA Transfection in Neoplastic T-Cells

Approximately forty million human neoplastic HUT78 cells were suspended in 40 mls of complete medium (RPMI-1640 (Gibco, Grand Island, N.Y.) with 10% fetal calf serum (Gibco) and incubated at 37° for 5 hours. After incubation, the cells were washed with RPMI-1640 (lacking fetal calf serum) and aliquoted into 4 tubes (approximately 10 million cells/tube) for transfection. Four mls of RPMI-1640, 50 mM Tris (pH 7.4), and 10 micrograms recombinant phage DNA containing the complete provirus HIV-$2_{SBL/ISY}$ was then added to each tube. Subsequently, 1 ml of 5×DEAE Dextran (25 mg/ml 100×) in RPMI-1640, 1M Tris (pH 7.4), was added to each tube. The tubes were incubated at 37° for 1 hour with gentle shaking. After incubation, the cells were pelleted at 1500 rpm and washed twice at room temperature with complete medium. The following day 10 mls of fresh complete media was added.

Viral production in the treated cells was monitored by testing the cell cultures for magnesium dependent reverse transcriptase (RT) one week post-transfection. To do so, proteins expressed by the cells into the supernatant were precipitated with 30% PEG, 0.4M NaCl, and the resulting pellets were resuspended in VSB as described by Rosenberg & Baltimore (J. Exp. Med. 147:1126–1141 (1978)). Reverse transcriptase was found based on the formation of precipitable counts of incorporated Tritium.

D. Immunofluorescence on Infected Cells

HIV-infected cells were pelleted, fixed on slides with 50% methanol:50% acetone for 10 minutes and incubated with 15 µl of human serum, obtained from individuals infected with HIV-2 and diluted 1:40 with PBS, for 30 minutes at room temperature. The slides were then washed with PBS and incubated with fluorescinated anti-human antibodies for 30 minutes. The positive cells were scored under a UV light microscope.

Electromicroscopy analysis on the HIV-2$_{SBL/ISY}$ transfected cells was performed as described by Biberfeld et al. (J. Natl. Can. Inst. 79:933–941 (1987)) and as shown in FIG. 2. The analysis revealed the presence of mature virions with the expected cylindrical shaped core typical of lentiviruses and budding particles from the cell membrane (see insert in FIG. 2), indicating that transfection of the HIV-2$_{SBL/ISY}$ DNA induced a productive infection in the HUT78 cell line.

Viral expression was confirmed by immunofluorescent staining of the infected cells using serum from an individual with HIV-2.

E. Infection of Target Cell Lines

The HUT78 cell line was expanded and HIV-2$_{SBL/ISY}$ virus was concentrated from about 10 liters of supernatant as described by Poiesz et al. in Proc. Natl. Acad. Sci. USA 77:7415–7419 (1980). The HIV-2$_{NIH-Z}$ isolate was employed for comparison in a parallel experiment. The equivalent of 1000 TCID50 infecting virus were used to infect human cell lines H9, MOLT-3, U937, HUT78, CEM, MT-2 and the T-cell clone 55. Cell lines H9, Molt-3, HUT78 and CEM are available through the ARRRP. T-cell clone 55 is available through Dr. Robert Gallo's Laboratory (Bethesda, Md.). The U937 and MT-2 cell lines were gifts made available to us for research purposes.

Approximately 5×10$^6$ cells from each cell line were treated with polybrene (Sigma, St. Louis, Mo.) at 5 µg/ml for 1 hour. The cells were washed with PBS then incubated for 1 hour with virus. At the end of the incubation period, the cells were again washed and resuspended in complete medium. Replication and propagation of the virus was monitored by reverse transcriptase activity in the culture supernatant and by immunofluorescence on fixed cells as described previously. The biological effect exerted on the infected cells by the HIV-2 isolates was measured by counting the number of viable cells and syncytia at different time intervals. Immunofluorescence and RT activity for each culture was measured every 3 days. Cell viability was calculated by subtracting the number of cells which incorporated trypan blue stain from those which did not. The number of syncytia was counted under a light microscope.

The detailed results of these experiments are reported below in Table 1 for the HIV-2$_{SBL/ISY}$ isolate.

TABLE 1

| HIV-2$_{SBL/ISY}$ infection | | Days in Culture | | |
|---|---|---|---|---|
| | | 5 | 8 | 12 |
| MT-2 | % IFA positive | ND | 20 | 32 |
| | RT | 16 | 16 | 29 |
| | Syncytia | + | ++ | ++ |
| | % Viable cells | 80 | 61 | 47 |
| CL55 | % IFA positive | ND | 10 | 25 |
| | RT | 6 | 28 | 14 |
| | Syncytia | + | ++ | +++ |
| | % Viable cells | 70 | 40 | 36 |
| CEM | % IFA positive | ND | 4 | 18 |
| | RT | 7 | 9 | 12 |
| | Syncytia | − | + | + |
| | % Viable cells | 98 | 76 | 71 |
| HUT78 | % IFA positive | 2 | 4 | 18 |
| | RT | 13 | 10 | 36 |
| | Syncytia | − | + | ++ |
| | % Viable cells | 90 | 71 | 50 |
| U937 | % IFA positive | 3 | ND | 12 |
| | RT | 8 | 76 | 41 |
| | Syncytia | − | ND | ND |
| | % Viable cells | 85 | 78 | 71 |
| H9 | % IFA positive | ND | 10 | 20 |
| | RT | 18 | ND | 90 |
| | Syncytia | + | ++ | +++ |
| | % Viable cells | 83 | 63 | 41 |
| MOLT 3 | % IFA positive | ND | 8 | 15 |
| | RT | 9 | 18 | 49 |
| | Syncytia | + | ++ | +++ |
| | % Viable cells | 77 | 53 | 43 |

IFA = immunofluorescence assay
RT = cpm × 10$^3$
Syncytia = +
% Viable Cells = percentage of cells that do not incorporate Trypan blue.

In addition to the results shown above, both HIV-2$_{SBL/ISY}$ and HIV-2$_{NIH-Z}$ infected the HTLV-I transformed T-cell line MT-2, the T-cell clone 55 (which is immortalized by a single defective copy of HTLV-I), and the CEM, HUT78, MOLT3, H9 and U939 neoplastic cell lines. The parental virus HIV-2$_{SBL6669}$ infects HUT78, U937 clone 16, CEM, and Jurkat T-cells.

Figure 4A:
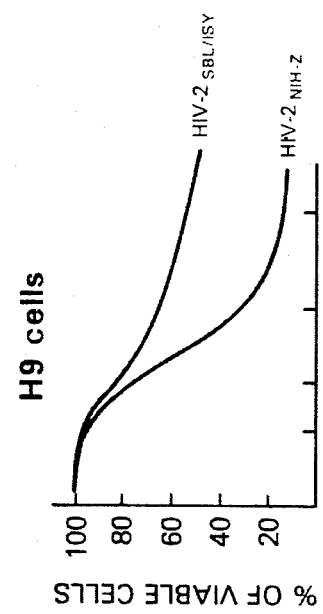
FIGS. 4a–c. Analysis of syncytia present in the cell culture. The left part of the figure graphically represents the reduction of the number of viable cells in culture after infection with the HIV-$2_{NIH-Z}$ and HIV-$2_{SBL/ISY}$ isolates. The pluses represent the relative scale of number of syncytia seen in the cell culture at 3, 5, 8 and 12 days. One example of the size of syncytia serum at day 8 with both the viral isolates is shown on the right of the figure.
Figure 4B:
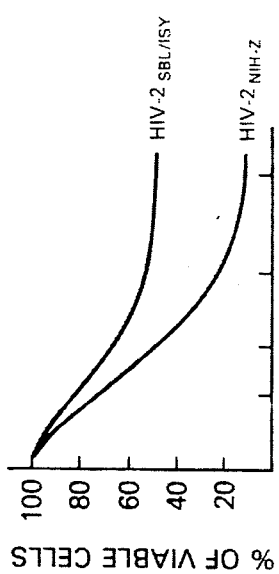
Figure 4C:
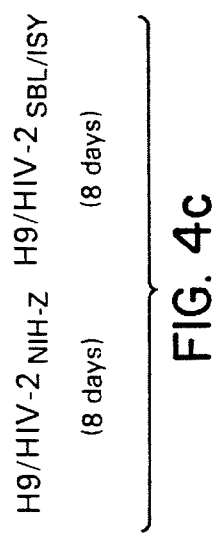

The highest cytopathic effect exerted by both HIV-2$_{SBL/ISY}$ and HIV-2$_{NIH-Z}$ was observed in the HTLV-I infected cells and in the H9 cells, a result which also coincides with the highest number of syncytia present in the cell culture (FIG. 4). The parental virus HIV-2$_{SBL666}$ exerted the highest cytopathic effect on the Jurkat and U937-16 cell lines as depicted in Table 2, below.

TABLE 2

| HIV-2$_{SBL666}$ infection | | Days in Culture | | | |
|---|---|---|---|---|---|
| | | 4 | 7 | 11 | 14 |
| Jurkat | RT | 13 | 12 | 70 | 213 |
| | Syncytia | + | ++ | +++ | +++ |
| HUT78 | RT | 3 | 20 | 176 | 155 |
| | Syncytia | + | + | + | +++ |
| U937-16 | RT | 17 | 8 | 80 | 279 |
| | Syncytia | + | +++ | +++ | +++ |

RT = cpm × 10$^3$
Syncytia = +

F. Western Blot Analysis

HUT78 T-cells infected with replication competent HIV-2$_{SBL/ISY}$ proviral DNA and SIV$_{mac}$ were pelleted and the supernatants removed and centrifuged at 20000 rpm for 1 hour to pellet the virus. These pellets were then resuspended in 1X RIPA buffer (5 mM PMSF, 75 mM NaCl, 25 mM Tris - pH 7.5, 0.5% SD, 5% tritonX- 100, 5% deoxycholic acid) in order to lyse the unlabelled virions for loading and electrophoresis on a 10% SDS PAGE gel. The gel was electrophoresed, the protein transferred to nitrocellulose filters, and the filters reacted with 5% dry milk in PBS for 1 hour as described by Towbin in Proc. Natl. Acad. Sci. USA 76:4350–4353 (1979).

Following the above-treatment, the filters were hybridized with: normal human serum (NS); serum from a macaque infected with $SIV_{mac}$ (1); sera from humans infected with HIV-2 (2 and 3); control mouse ascite (C); mouse monoclonal antibody directed against the HIV-2/$SIV_{mac}$ major gag protein (p24-26) of SIV (F5). Iodinated Staohylococcus aureus protein-A was used to detect immunocomplexes. The results are shown in FIG. 3.

The most reactive and apparently also the most abundant viral proteins detected in the HIV-2$_{SBL/ISY}$ and $SIV_{mac}$ virions were the gag p24-26 and p15 proteins (first two panels of FIG. 3). Similar results were obtained when radiolabelled HIV-2$_{SBL/ISY}$ virion proteins were used in a radioimmunoprecipitation (RIP) assay (left panel of FIG. 3). The envelope glycoprotein gp120 was barely detected by immunoprecipitation and not at all by Western blots.

The DNA sequence of the replication competent proviral clone lacks a termination codon in the transmembrane portion of the envelope gene and should yield a transmembrane envelope glycoprotein of around 40Kd. Indeed, a very faint band around 40Kd could be detected in RIP or Western blot assays of HIV-2$_{SBL/ISY}$ using positive human sera. A smear, probably representing proteins with different relative migration rates, was detected around 30Kd in $SIV_{mac}$. This smear is believed to be the truncated form of the transmembrane protein, although the amino acid sequence after the termination codon is expressed in infected animals.

G. Immunoprecioitation of Viral Proteins

Cells infected with HIV-2$_{SBL/ISY}$ of SIV were incubated in RPMI media supplemented with $^{35}$S-methionine and $^{35}$S-cystein (100 μCi/ml) for 4 hours, pelleted and the supernatants centrifuged at 20,000 rpm for 1 hour to pellet the labelled virus. The labelled lysate was pre-cleared overnight with normal human sera and sepharose bound protein-A. Aliquots of the pre-cleared lysates were incubated with sera from HIV-2-infected humans or SIV-infected monkeys and the immunocomplexes were isolated with Staphylococcus aurueus protein-A bound to sepharose. The samples were electrophoresed on a 10% SDS PAGE and the gel was treated with enhancer (Dupont, Boston, Mass. ) for 30 minutes, dried and autoradiographed. The results are shown in FIG. 3.

We claim:

1. An isolated and purified replication competent HIV-2 proviral clone designated HIV-2$_{SBL/ISY}$.

2. The clone of claim 1 wherein said clone has the restriction profile as shown in FIG. 1.

3. An isolated and purified DNA segment having the nucleotide sequence or a nucleotide sequence encoding one or more of the amino acid sequences as shown in FIG. 5.

* * * * *